US012241889B2

(12) United States Patent
Sluka

(10) Patent No.: US 12,241,889 B2
(45) Date of Patent: Mar. 4, 2025

(54) MALATE TO DETECT AND AS A TARGET FOR FIBROMYALGIA

(71) Applicant: University of Iowa Research Foundation, Iowa City, IA (US)

(72) Inventor: Kathleen A. Sluka, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 377 days.

(21) Appl. No.: 17/464,335

(22) Filed: Sep. 1, 2021

(65) Prior Publication Data

US 2022/0065846 A1 Mar. 3, 2022

Related U.S. Application Data

(60) Provisional application No. 63/073,314, filed on Sep. 1, 2020.

(51) Int. Cl.
*G01N 33/52* (2006.01)
*G01N 33/573* (2006.01)

(52) U.S. Cl.
CPC ........... *G01N 33/52* (2013.01); *G01N 33/573* (2013.01)

(58) Field of Classification Search
CPC .............................. G01N 33/52; G01B 33/573
See application file for complete search history.

(56) References Cited

PUBLICATIONS

Wright, Cheryl L et al. "Duloxetine for the treatment of fibromyalgia." Expert review of clinical immunology vol. 6,5 (2010): 745-56. doi:10.1586/eci.10.64 (Year: 2010).*

Ahmad, Faraz et al. "Simple, reliable, and time-efficient colorimetric method for the assessment of mitochondrial function and toxicity." Bosnian journal of basic medical sciences vol. 18,4 367-374. Nov. 7, 2018, doi:10.17305/bjbms.2018.3323 (Year: 2018).*

Khoonsari, Payam Emami et al. "Systematic analysis of the cerebrospinal fluid proteome of fibromyalgia patients" Journal of Proteomics vol. 190 (2019), p. 35-43. https://doi.org/10.1016/j.jprot.2018.04.014. (Year: 2019).*

Parveen, Ifat et al. "Application of gas chromatography-mass spectrometry metabolite profiling techniques to the analysis of heathland plant diets of sheep." Journal of agricultural and food chemistry vol. 55,4 (2007): 1129-38. doi:10.1021/jf062995w (Year: 2007).*

D'Agnelli S, et al. Fibromyalgia: Genetics and epigenetics insights may provide the basis for the development of diagnostic biomarkers. Molecular Pain. 2019;15. doi:10.1177/1744806918819944 (Year: 2018).*

Ribeiro, V G C et al. "Inflammatory biomarkers responses after acute whole body vibration in fibromyalgia." Brazilian journal of medical and biological research = Revista brasileira de pesquisas medicas e biologicas vol. 51,4 e6775. Mar. 1, 2018, doi:10.1590/1414-431X20176775 (Year: 2018).*

Arts, Rob J W et al. "Glutaminolysis and Fumarate Accumulation Integrate Immunometabolic and Epigenetic Programs in Trained Immunity." Cell metabolism vol. 24,6 (2016): 807-819. doi:10.1016/j.cmet.2016.10.008 (Year: 2016).*

Banfi et al. T Cell Subpopulations in the Physiopathology of Fibromyalgia: Evidence and Perspectives. Int J Mol Sci. Feb. 2020; 21(4): 1186. Published online Feb. 11, 2020. doi: 10.3390/ijms21041186 (Year: 2020).*

DeSantana JM, da Cruz KM, Sluka KA. Animal models of fibromyalgia. Arthritis Res Ther. 2013;15(6):222. doi: 10.1186/ar4402. PMID: 24314231; PMCID: PMC3979153. (Year: 2013).*

* cited by examiner

*Primary Examiner* — Gregory S Emch
*Assistant Examiner* — Mckenzie A Dunn
(74) *Attorney, Agent, or Firm* — Schwegman Lundberg & Woessner, P.A.

(57) ABSTRACT

Methods of detecting malate, and monitoring fibromyalgia, are provided.

20 Claims, 14 Drawing Sheets

QEGC_MALATE_CONTROL

QEGC_FUMARATE_FM

QEGC_FUMARATE_CONTROL

ISO_MALATE_CONTROL

ISQ_FUMARATE_FM

ISO_FUMARATE_CONTROL

MALATE TO DETECT AND AS A TARGET FOR FIBROMYALGIA

CROSS-REFERENCE TO RELATED APPLICATIONS

This application claims the benefit of the filing date of U.S. application No. 63/073,314, filed on Sep. 1, 2020, the disclosure of which is incorporated by reference herein.

BACKGROUND

Fibromyalgia (FM) is a complex condition characterized by widespread pain and fatigue. A recent meta-analysis of 65 studies that included more than 3 million people worldwide showed the prevalence of FM is approximately 2% overall and 4% in women (Heidari et al., 2017). Pharmacological interventions are modestly effective for FM with most individuals experiencing activity-limiting pain and fatigue despite the use of multiple drugs (Okifuji and Hare, 2013; Vincent et al., 2015). A recent population-based study reported that 22% of FM patients were using chronic opioids and 19% were using chronic benzodiazepines (Vincent et al., 2015). Fibromyalgia is diagnosed based on reported symptoms, using established criteria that focus on widespread pain, fatigue, sleep dysfunction and cognitive dysfunction (Wolfe, 2011; Wolfe et al., 2016); as there are no validated chronic pain biomarkers to assist with diagnosis, or treatment evaluation endpoints. Diagnosing FM often takes years with patients seeing multiple different physicians, which delays treatment. A recent survey of 800 people with FM and 1622 physicians showed that it took an average of 2.3 years and 3.7 physicians before receiving a FM diagnosis (Choy et al., 2010). Despite established symptom-based diagnostic criteria for FM, there is still skepticism in the medical community about the existence of the disease (Hauser & Fitzcharles, 2018).

SUMMARY

As disclosed herein, potential biomarkers in individuals with FM were identified and correlated with FM symptoms using an untargeted metabolomics approach. For example, plasma samples and baseline patient-reported outcomes for resting pain and fatigue were analyzed from 59 women with FM (mean±SD; age=49.69±11.54, BMI=35.23±10.91) matched with 38 healthy controls (HC) (age=51.0±11.46, BMI=32.33±8.66). Serum/plasma metabolomic extracts were derivatized and analyzed by gas chromatography mass spectrometry for 63 key metabolites representing the tricarboxylic acid cycle, glycolysis, pentose phosphate pathway, amino acid metabolism, neurotransmission, reactive oxygen species defense, and energetics.

In one embodiment, 18 candidate biomarkers were identified using a semi-targeted metabolomics approach in plasma samples from women with FM (n=59) and matched healthy controls (n=38). Several of the 63 metabolites screened differed between cohorts, suggesting the potential role of altered metabolic pathways in FM. One metabolite in particular, malate, showed excellent sensitivity (>90%) and specificity (>90%) in identifying FM with nearly complete separation from healthy controls. The concentrations of malate in healthy controls were 1652+183 (mean+SD; range 1294-2090) and those of fibromyalgia were 616+153 (range 408-1437) (P<0.0001). One subject fell within the range of the healthy controls. Malate strongly correlated with pain (r=−0.894, p=0.0001) and fatigue (r=−0.880, p=0.0001) (FIG. 1). In one embodiment, fibromyalgia patients have levels of malate that are reduced by at least 10%, 20%, 30%, 40%, 50% or more relative to control patients that do not have fibromyalgia. Malate was confirmed as a potential biomarker using a separate colorimetric analysis of the samples, and in a smaller cohort of individuals with FM. Other metabolites that may be employed instead of or in various combinations with malate including but not limited to fumarate, cysteine, and 6-phosphogluconate. In one embodiment, a colorimetric assay is employed to detect malate. For example, malate dehydrogenase catalyzes the oxidation of malate in which the formed NADH reduces a formazan (MTT) reagent. The intensity of the product color, measured at 565 nm, is proportional to the malate concentration in the sample, e.g., using standard curves.

In one embodiment, a method to diagnose fibromyalgia in a mammal is provided. The method includes determining the amount or presence of malate or fumarate in a physiological sample, e.g., physiological fluid sample from the mammal. In one embodiment, a decrease in relative malate amounts, e.g., relative to a control, is indicative of fibromyalgia. In one embodiment, the mammal is a human. In one embodiment, the sample is a blood sample. In one embodiment, the sample is a plasma sample. In one embodiment, the sample is a serum sample. In one embodiment, the amount of presence or malate is determined using an enzymatic assay. In one embodiment, the amount of malate that is indicative of fibromyalgia is below 1500, e.g., below 1200, units. In one embodiment, the amount of malate in blood that is indicative of fibromyalgia is below 20 μM, e.g., below 10 μM. In one embodiment, the amount of malate in blood or plasma that is indicative of fibromyalgia is below $2\times10^{-6}$ g/$cm^3$, e.g., below $1\times10^{6}$ g/$cm^3$. In one embodiment, the amount of fumarate in the sample is below 1100 units or is less than 1 μM, e.g., less than 0.5 μM. In one embodiment, the amount of malate and at least one of fumarate, cysteine, or 6-phosphogluconate is detected. In one embodiment, the malate is detected using a colorimetric assay. In one embodiment, the sample is subjected to mass spectrometry or chromatography prior to detecting the amount or presence of malate. In one embodiment, mass spectrometry or chromatography is employed to detect the amount or presence of malate.

In one embodiment, a method to distinguish pain resulting from fibromyalgia from other disorders is provided. The method includes determining the amount or presence of malate or fumarate in a physiological sample from a mammal having pain; and comparing the amount or presence of malate in the sample to the amount of malate in a corresponding mammal that does not have fibromyalgia, wherein decreased levels of malate in the mammal having pain is indicative that the mammal has pain due to fibromyalgia. In one embodiment, the mammal is a human. In one embodiment, the sample is a blood sample. In one embodiment, the sample is a plasma sample. In one embodiment, the sample is a serum sample. In one embodiment, the amount or presence of malate is determined using an enzymatic assay. In one embodiment, the amount of malate in the sample is determined to be below 1200 units or below 10 μM. In one embodiment, the amount of fumarate in the sample is below 1100 units or is less than 1 μM, e.g., less than 0.5 μM. In one embodiment, the amount of malate and at least one of fumarate, cysteine, or 6-phosphogluconate is determined. In one embodiment, the malate is determined using a colorimetric assay. In one embodiment, the sample is subjected to mass spectrometry or chromatography prior to determining the amount of malate. In one embodiment, mass spectrometry or chromatography is employed to determine the amount of malate. The use of an assay to detect malate may allow for a determination that the mammal, e.g., a human has fibromyalgia rather than, for example, chronic fatigue syndrome, Long-COVID, or post-traumatic stress disorder, which may have higher, e.g., closer to normal, levels of malate.

Also provided is a method of monitoring fibromyalgia progression or severity in a mammal, comprising determining the amount of malate in a physiological sample from a mammal having fibromyalgia over time; and comparing the amount of malate over time in the mammal having fibromyalgia to the amount of malate in a corresponding mammal without fibromyalgia. In one embodiment, the mammal is a human. In one embodiment, the sample is a blood sample. In one embodiment, the sample is a plasma sample. In one embodiment, the sample is a serum sample. In one embodiment, the amount or presence of malate is determined using an enzymatic assay. In one embodiment, the amount of malate in the sample is determined to be below 1200 units or below 10 μM. In one embodiment, the amount of fumarate in the sample is below 1100 units or is less than 1 μM, e.g., less than 0.5 μM. In one embodiment, the amount of malate and at least one of fumarate, cysteine, or 6-phosphogluconate is determined. In one embodiment, the malate is determined using a colorimetric assay. In one embodiment, the sample is subjected to mass spectrometry or chromatography prior to determining the amount of malate. In one embodiment, mass spectrometry or chromatography is employed to determine the amount of malate.

Further provided is a method of inhibiting or treating pain in a mammal, comprising: determining whether a mammal with pain has decreased malate levels; administering to the mammal having pain and decreased levels of malate an effective amount of duloxetine, amitriptyline, pregabalin, trazodone, meloxicam, gualfenesin, topamax, armodafinil, prednisone, milnacipran, topiramate, escitalopram, naltrexone, venlafaxine, metaxalone, fluoxetine, sodium oxybate, atomoxetine, desvenlafaxine, Desyrel dividose, topiragen or metaxail. In one embodiment, the mammal is a human. In one embodiment, the sample is a blood sample. In one embodiment, the sample is a plasma sample. In one embodiment, the sample is a serum sample. In one embodiment, the amount or presence of malate is determined using an enzymatic assay. In one embodiment, the amount of malate in the sample is determined to be below 1200 units or below 10 μM. In one embodiment, the amount of fumarate in the sample is below 1100 units or is less than 1 μM, e.g., less than 0.5 μM. In one embodiment, the amount of malate and at least one of fumarate, cysteine, or 6-phosphogluconate is determined. In one embodiment, the malate is determined using a colorimetric assay. In one embodiment, the sample is subjected to mass spectrometry or chromatography prior to determining the amount of malate. In one embodiment, mass spectrometry or chromatography is employed to determine the amount of malate. Once diagnosed with pain due to fibromyalgia, a mammal such as a human may be administered a drug, such as duloxetine, milnacipran and/or pregabalin and optionally may be subjected to physical therapy, exercise as first-line treatments, and/or cognitive behavior therapy, which may be in contrast to a mammal that has pain not due to fibromyalgia.

In one embodiment, a method is provided comprising: determining whether a mammal has decreased malate levels relative to a corresponding control mammal; and administering to a mammal having decreased malate levels an amount of Lyrica, Cymbalta, gabapentin, savella, tramadol, cyclobenzaprine, duloxetine, milnacipran, amitriptyline, pregabalin, trazodone, meloxicam, gualfenesil, topamax, armodafinil, dresaryl, nabilone, prednisone, topiramate, escitalopram, naltrexone, venlafaxine, metaxalone, fluoxetine, sodium oxybate, atomoxetine, desvenlafaxine, Desyrel dividose, topiragen or metaxail. In one embodiment, the mammal is a human. In one embodiment, the sample is a blood sample. In one embodiment, the sample is a plasma sample. In one embodiment, the sample is a serum sample. In one embodiment, the amount or presence of malate is determined using an enzymatic assay. In one embodiment, the amount of malate in the sample is determined to be below 1200 units or below 10 μM. In one embodiment, the amount of fumarate in the sample is below 1100 units. In one embodiment, the amount of malate and at least one of fumarate, cysteine, or 6-phosphogluconate is determined. In one embodiment, the malate is determined using a colorimetric assay. In one embodiment, the sample is subjected to mass spectrometry or chromatography prior to determining the amount of malate. In one embodiment, mass spectrometry or chromatography is employed to determine the amount of malate.

DETAILED DESCRIPTION

Figure 1:
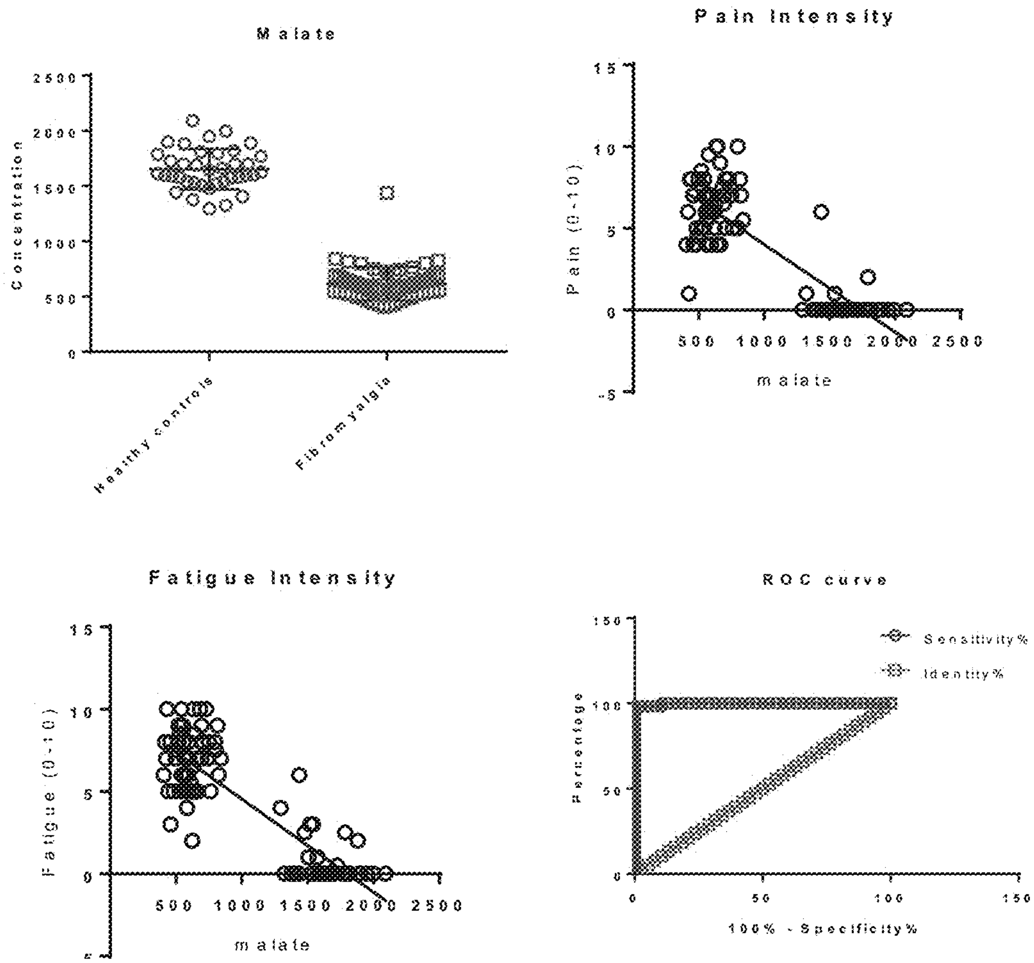
FIG. 1. The first graph shows a scatter plot with means and SD for malate concentrations (arbitrary units) in healthy controls (blue) and individuals with fibromyalgia (red) ($p<0.0001$). The two scatter plots show the correlation between pain intensity and malate, and fatigue intensity and malate. The final graph shows the ROC curve for malate (AUC=0.998).

Fibromyalgia (FM) is difficult to diagnose and treat with current approaches based primarily on symptoms. The delayed diagnosis and treatment initiation for FM would be dramatically reduced with the identification of clear biomarkers for FM. Biomarkers have been defined as an indicator of a biological or pathogenic process, and can be useful to examine disease severity, develop therapeutic targets, or assess effects of a therapy. Thus, biomarkers for FM improve the diagnosis and/or development of therapeutic targets for individuals with widespread pain. As disclosed herein, candidate metabolic biomarkers were assessed to diagnose fibromyalgia and evaluate the relationships between metabolic biomarkers and fibromyalgia symptoms. These biomarkers allow for diagnostic tests and screening of therapeutics to improve outcomes for individuals with FM.

Biomarkers have been defined as accurate and reproducible indicators of biological or pathogenic processes and are increasingly being used to characterize disease severity or as primary endpoints to assess treatment effects (Group BDW, 2001; Strimbu & Tavel, 2010). Biomarkers have the potential to predict clinical outcomes and may be useful as targets to enhance precision medicine. Treatment of individuals with FM may be improved by targeting specific pain mechanisms that underlie the observed symptoms. Biomarkers not only provide an opportunity to assist with diagnosis of a disease but may be used to understand pain mechanisms and develop new therapeutic targets. Understanding the role of multiple biomarkers in identifying individuals with FM, and their relationships with multiple outcome domains, provides for an improved ability to characterize underlying mechanisms, advance diagnostic criteria, and provide potential therapeutic targets. In other patient populations, e.g., Diabetes Mellitus, classification by underlying mechanisms has long been used to direct and optimize treatment. The first step to establish a biomarker is the characterization of the sensitivity, specificity, selectivity, and stability of the marker for the condition. A biomarker for FM has specificity to FM compared to other chronic pain conditions.

The most accepted underlying mechanism of FM is altered central nervous system processing of nociception and pain (Sluka & Clauw, 2016; Clauw, 2014). Additional studies show alterations in the immune system, and small fiber neuropathy in people with FM (Sluka & Clauw, 2016; Mendieta et al., 2016; Uceyler et al., 2011; Serra et al., 2014; Uceyler et al., 2013; Oaklander & Herzog, 2013). However, these have not led to biomarkers with good sensitivity and specificity, suggesting either multiple underlying mechanisms underlie FM or additional mechanisms are involved. Further, it is unclear if the observed alterations in the central nervous system, immune system, and small fiber neuropathy are causative, or a consequence of yet undiscovered phenomena. Current treatments are based on clinical trials that show non-specific efficacy in the population and include a mixture of pharmacological and non-pharmacological approaches (Macfarlane et al., 2017). Pharmacological interventions are modestly effective for FM with most individuals continuing to experience activity-limiting pain and fatigue despite use of multiple drugs (Okifuji & Hare, 2013; Vincent et al., 2015). The lack of clear symptomology biomarkers limits the ability for clinicians to utilize precision medicine. Thus, there is a need for validation of disease-specific and symptomology biomarkers to assist with diagnosis, promote targeted treatments, and develop future therapeutic targets that provide more effective symptom relief.

Figure 2:
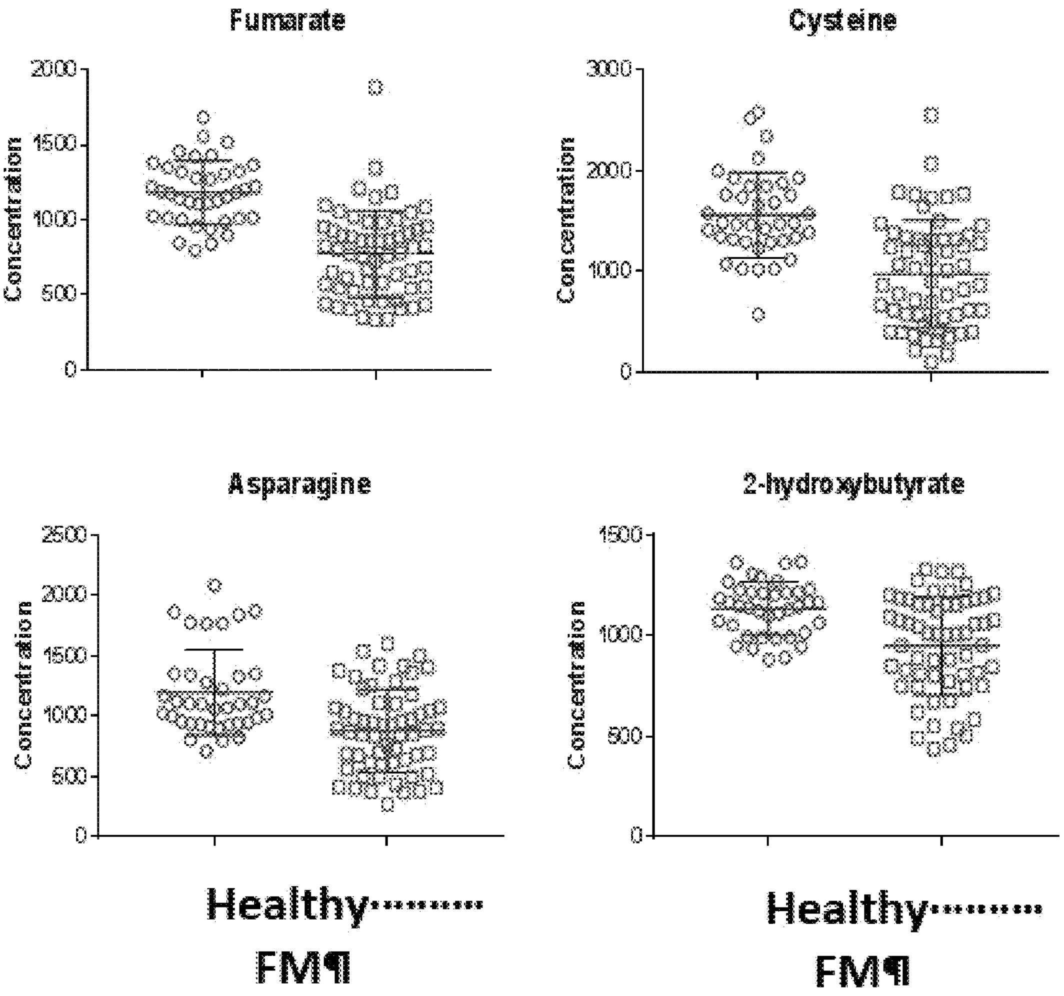
FIG. 2. Scatter plot with means (SD) for fumarate, cysteine, asparagine and 2-hydroxybutyrate in healthy controls (blue) and individuals with fibromyalgia (red). Each metabolite shows significant differences between FM and HC ($p<0.001$).

Metabolomics is an area of study that is increasingly recognized as playing key roles in multiple disease states (Dunn et al., 2013). A metabolite is any small molecule that serves as an intermediate or end-product of metabolism, including amino acids, Krebs Cycle fuels, metabolic signaling intermediates, or allosteric enzyme activity modulator, to name a few. There are several metabolites that differ substantially in individuals with FM compared to age-, sex- and BMI-matched HCs. Initially, an exploratory analysis to identify potential metabolite biomarkers was performed in individuals with FM from a recently completed clinical trial on transcutaneous electrical stimulation (TENS), compared to healthy controls (HC) using a targeted metabolomics approach. Baseline plasma samples and baseline patient-reported outcomes for resting pain and fatigue were analyzed from 59 women with FM (mean f SEM; age=49.7±11.5 yr, BMI=35.2±10.9 kg/m$^2$) and 38 healthy women (age=51.0±11.5 yrs, BMI=32.3±8.7 kg/m$^2$). Plasma metabolite extracts were derivatized and analyzed by ISQ single quadrapole gas chromatography mass spectrometry for 63 key metabolites representing the tricarboxylic acid cycle, glycolysis, pentose phosphate pathway, amino acid metabolism, neurotransmission, reactive oxygen species defense, and energetics Several metabolites were significantly different between cohorts, but one in particular, malate, is dramatically less in women with FM (FIG. 1). The concentrations of malate in HCs were 1652±183 (arbitrary units, mean f SD; range 1294-2090) and those of FM were 616±153 (range 408-1437) ($P<0.0001$). The scatter plot of this data shows only one subject with FM fell within the range of the HCs (FIG. 2). In one embodiment malate concentrations in blood in normal humans is about 15 to 30, e.g., 12-25, μM or about 3-6×10$^{-6}$ g/cm$^3$ and in plasma about 1-9×10$^{-6}$ g/cm$^3$. In one embodiment, malate concentrations in blood in a human with fibromyalgia are about 1 to 15, e.g., 5 to 10, μM, or about 0.4-2.5×10$^{-6}$ g/cm$^3$ and in plasma about 0.33-0.5×10$^{-6}$ g/cm$^3$ or less than about 1×10$^{-6}$ g/cm$^3$. In one embodiment malate concentrations in blood in normal humans are about 20 μM or about 4.6×10$^{-6}$ g/cm$^3$ and in plasma about 1-9×10$^{-6}$ g/cm$^3$. In one embodiment, malate concentrations in blood in a human with fibromyalgia are about 7.4 μM or about 1.7×10$^{-6}$ g/cm$^3$ and in plasma about 0.33-3×10$^{-6}$ g/cm$^3$.

The Receiver Operating Characteristic (ROC) curve resulted in an area under the curve (AUC) of 0.998 (0.994-1.0; 95% CI) for malate (FIG. 2), demonstrating high sensitivity and specificity of malate for identifying FM. To test for assay repeatability, two additional processing methods were evaluated: plasma samples were run with high resolution QE-GC orbitrap mass spectrometry for all 63 metabolites and malate alone was assessed with a colorimetric assay. Similar results were obtained with both assays for malate, showing a correlation coefficient of $R=0.71$ ($p<0.0001$).

Figure 3:
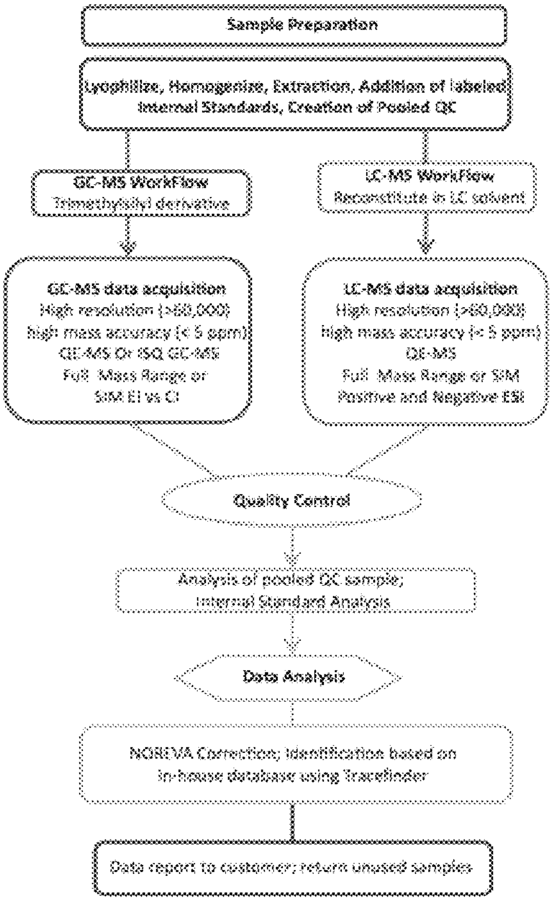
FIG. 3. Flowchart of Metabolomics Core analysis workflow. Samples are received and prepared by Core staff and go through either or both GC-MS (proposed analysis) and LC-MS workflow.

Malate is involved in energy metabolism as part of the Krebs cycle and is important in aerobic metabolism of nearly all cells. One of the major reactions occurring in this cycle is the reversible hydration of fumarate to malate. This is a transition step in the production of energy through the reduction of NAD+ to NADH. Importantly, significantly less fumarate was found in those with FM: (773±37 FM; 1182±34 HC, $p<0.0001$, FIG. 3). The ROC curve for fumarate resulted in an AUC=0.82 (0.82-0.95; 95% CI). Several other metabolites involved in this process were also identified as significantly different between FM and HC, including: fumarate, cysteine, asparagine, aconitate, 2-hydroxybutyrate, 6-phosphogluconate, tryptophan, sphingosine, hypoxanthine, histidine, 1-octadecanol, uracil, inositol, phosphoenolpyruvate, xanthine, serine, and urea (see Table 1). These findings show a consistent pattern of impaired cellular energy metabolism in FM, suggesting a potentially novel mechanism underlying the disease. FIG. 3 shows scatter plots for 4 of these additional metabolites that differed in FM, but with smaller effect sizes than malate.

TABLE 1

Candidate metabolites for FM biomarkers.

| Metabolite | Pathway/ Description | ROC AUC | AUC $95^{th}$ CI | False Discovery Rate | FM:HC ratio | Effect sized |
|---|---|---|---|---|---|---|
| Malate | Intermediate in Citric Acid Cycle | 0.998 | .99-1.0 | <.0001 | 0.37 | −6.13 |
| Fumarate | Intermediate in Citric Acid Cycle | 0.888 | .82-.95 | <.0001 | 0.62 | −1.62 |
| Cysteine | Amino acid involved in glutamate, glycine, serine, glutathione metabolism | 0.806 | .72-.89 | <.0001 | 0.54 | −1.22 |
| 6-Phosphogluconate | Pentose phosphate pathway | 0.771 | .67-.87 | <.0001 | 1.20 | 0.93 |
| Sphingosine | Sphingolipid metabolism | 0.752 | .65-.85 | 0.000 | 1.31 | 0.81 |
| Hypoxanthine | Intermediate in purine metabolism | 0.748 | .64-.86 | 0.001 | 1.20 | 0.81 |
| Asparagine | Amino acid involved in protein biosynthesis | 0.730 | .63-.83 | <.0001 | 0.70 | −0.90 |
| Tryptophan | Amino acid precursor of serotonin and melatonin | 0.728 | .63-.83 | 0.000 | 0.83 | −0.86 |
| 2-Hydroxybutyrate | By-product of glutathione metabolism | 0.719 | .62-.82 | <.0001 | 0.81 | −0.94 |
| Histidine | Amino acid involved in multiple pathways | 0.686 | .58-.79 | 0.002 | 0.78 | −0.77 |
| Uracil | Beta-alanine metabolism | 0.685 | .58-.79 | 0.013 | 1.13 | 0.65 |
| 1-Octadecanol | Lipid and fatty acid metabolism | 0.680 | .57-.79 | 0.002 | 1.10 | 0.93 |
| Aconitate | Intermediate in Citric Acid Cycle | 0.675 | .56-.79 | 0.013 | 1.20 | 0.58 |
| Inositol | Carbocyclic sugar, involved in cell signaling | 0.666 | .56-.78 | 0.013 | 0.85 | −0.61 |
| Phosphoenolpyruvate | Gluconeogenesis and Glycolysis | 0.665 | .55-.78 | 0.021 | 1.09 | 0.58 |
| Urea | By-product of protein catabolism | 0.652 | .54-.77 | 0.050 | 0.87 | −0.44 |
| Serine | Amino acid involved in one-carbon metabolism and methylation | 0.651 | .54-.76 | 0.039 | 0.85 | −0.51 |
| Xanthine | Intermediate in purine metabolism | 0.642 | .53-.76 | 0.033 | 1.18 | 0.55 |

The possibility was considered that the results could be attributed to physical activity levels between individuals with FM and HCs since metabolites are inherently related to energy metabolism. However, there were similar activity levels between groups examined either with accelerometry or by self-report (International Physical Activity Questionnaire-short form, LPAQ). There were low correlations between the 17 identified metabolites that showed between cohort differences and physical activity levels ($r<0.17$ for MVPA; $r<0.14$ for IPAQ). Lastly, repeating the between cohort analyses adjusting for activity level (either with accelerometry or self-report outcomes) produced virtually no change in the between-group significance for malate ($p<0.0001$) or any of the other 17 metabolites showing between group differences.

The correlations between the putative metabolic biomarkers and several common FM symptoms were also assessed, finding moderate associations (see r values below, all $p<0.05$). Pain intensity (measured by the Brief Pain Inventory and numerical rating scale) correlates with: malate (0.23-0.24), serine (−0.27), and aconitate (0.22); fatigue (measured by the Multidimensional Assessment of Fatigue) correlates with: 6-phosphogluconate (0.24), uracil (0.21), urea (0.22), and xanthine (0.26); and the Fibromyalgia Impact Questionnaire-revised (FIQR) correlates with: 6-phosphoguconate (0.31); aconitate (0.22), fumarate (0.21), hypoxanthine (0.22), phosphoenolpyruvate (0.22), serine (−0.23) and xanthine (0.37). Thus, there were unique symptoms associated with different metabolites which may be useful for future therapeutic development or disease sub-classification.

Few studies have examined metabolomic profiles in individuals with FM. Using NMR metabolomics in a small group of female FM (n=19) compared to age- and sex-matched healthy controls (n=10) there are differences in hippuric, succinic, taurine, creatine, and lactic acid (Malatji et al., 2017). However, subjects were not matched for BMI and with the low sample size, the findings may not reflect the overall population and may be due to chance alone. Vibrational spectroscopy techniques have been applied to FM, in an attempt to differentiate this disease state from OA, RA, and most recently Lupus, but these do not yet result in reproducible metabolite concentrations that can serve as FM biomarkers (Hackshaw et al., 2013; Hackshaw et al., 2019). These studies, using relatively small sample sizes, show a unique spectral metabolic signature in those with FM, supporting the role of altered metabolites in FM; however, it is unclear which specific metabolites are involved. A third analysis examined metabolomics using Liquid Chromatography-Quadrupole-Time of Flight/Mass Spectrometry (LC-Q-TOF/MS) in FM (n=22) compared to healthy controls (n=21) and identified lipid compounds that were uniquely different between the groups (Caboni et al., 2014). This study however did not provide subject characteristics, determine if the metabolites were related to symptoms, and used a relatively small sample size. Thus, these studies demonstrate varied alterations in metabolic profiles with FM, in part supporting the underlying premise that systemic metabolites can be used for biomarkers.

In summary, biomarkers for FM were identified based on blood-derived metabolic profiles. The data showed there was a strong separation of metabolites, particularly malate, between individuals with FM and healthy controls using a relatively large sample size (n=59 FM; n=38 healthy controls). Malate has a ROC AUC of 0.998, demonstrating excellent sensitivity and specificity for identifying FM. An additional 17 metabolites were discovered using the targeted metabolomics approach to be significantly different between matched cohorts, with unique moderate correlations with FM symptomology, allowing for further exploration of other potential biomarkers.

The invention is will further described by the following non-limiting examples.

Example 1

It was hypothesized that modification of malate, e.g., malate levels, may affect symptoms of fibromyalgia, particularly pain and fatigue.

FIG. 1 shows a scatter plot with means and SD for malate in healthy controls (blue) and individuals with fibromyalgia (red). Two scatter plots show the correlation between pain intensity and malate, and fatigue intensity and malate. The other graph shows the ROC curve for malate.

The Received Operator Characteristics was 0.994 for malate and Cohen's d=6.3. Values for sensitivity and specificity of malate are given in Table 2. Note there are clear values that give 90-100% specificity (identify correctly those without the diagnosis) with 90-100%/o sensitivity (identify those with the diagnosis).

TABLE 2

| Malate Value | Sensitivity % | 95% CI | Specificity % | 95% CI |
|---|---|---|---|---|
| <703.9 | 81.36 | 69.09% to 90.31% | 100 | 90.75% to 100% |
| <716.5 | 83.05 | 71.03% to 91.56% | 100 | 90.75% to 100% |
| <735.5 | 84.75 | 73.01% to 92.78% | 100 | 90.75% to 100% |
| <745.5 | 86.44 | 75.02% to 93.96%l | 100 | 90.75% to 100% |
| <755.1 | 88.14 | 77.07% to 95.09% | 100 | 90.75% to 100% |
| <779.8 | 89.83 | 79.17% to 96.18% | 100 | 90.75% to 100% |
| <799.5 | 91.53 | 81.32% to 97.19% | 100 | 90.75% to 100% |
| <808.2 | 93.22 | 83.54% to 98.12% | 100 | 90.75% to 100% |
| <820 | 94.92 | 85.85% to 98.94% | 100 | 90.75% to 100% |
| <832.3 | 96.61 | 88.29% to 99.59% | 100 | 90.75% to 100% |
| <1068 | 98.31 | 90.91% to 99.96% | 100 | 90.75% to 100% |
| <1309 | 98.31 | 90.91% to 99.96% | 97.37 | 86.19% to 99.93% |
| <1350 | 98.31 | 90.91% to 99.96% | 94.74 | 82.25% to 99.36% |
| <1391 | 98.31 | 90.91% to 99.96% | 92.11 | 78.62% to 98.34% |
| <1421 | 98.31 | 90.91% to 99.96% | 89.47 | 75.2% to 97.06% |
| <1439 | 100 | 93.94% to 100% | 89.47 | 75.2% to 97.06% |
| <1460 | 100 | 93.94% to 100% | 86.84 | 71.91% to 95.59% |
| <1492 | 100 | 93.94% to 100% | 84.21 | 68.75% to 93.98% |
| <1513 | 100 | 93.94% to 100% | 81.58 | 65.67% to 92.26% |

Malate is involved in energy metabolism and part of the Krebs cycle and is important in metabolism of nearly all aerobic cells. One of the major reactions occurring in this cycle is the reversible hydration of fumarate to malate. This is a transition step in the production of energy in the form of NADH. Importantly significant differences were found in fumarate using the metabolomic approach: (773+37 FM; 1182+34 HC, p<0.0001). The ROC curve for fumarate was 0.82. Several other metabolites involved in this process were also identified as significantly different between FM and HC.

However, the finding with the greatest result and most specificity and sensitivity was malate.

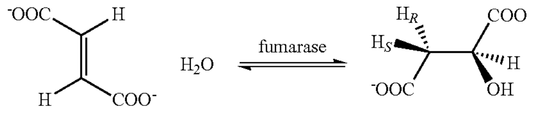

Fumarate

S-malate

Malate is also used in a malate-aspartate shuttle during glycolysis across the inner membrane of the mitochondria for oxidative phosphorylation, and is thus involved in the oxidation-reduction process for the formation of ATP. ATP is the main energy source of cells. Malate dehydrogenase enzyme is the primary enzyme in the shuttle.

Thus, the alterations in malate may lead to the symptoms associated with fibromyalgia which is evidenced by the strong correlations between pain and fatigue.

With the nearly full separation between fibromyalgia and healthy controls malate could be a diagnostic test for identification of individuals with fibromyalgia. This greatly enhances the understanding of the disease, improves acceptance in the health care community, and helps target treatments to those with fibromyalgia. a simple assay to test malate in plasma that can be used clinically.

Example 2

Malate is involved in aerobic energy metabolism, as a key metabolite in the citric acid (Kreb's) cycle. Malate is an intermediary in the cycle; produced from the reversible hydration of fumarate, followed by reversible oxidation to oxaloacetate resulting in energy production in the form of NADH (nicotinamide adenine dinucleotide+hydrogen). The alterations in malate may lead to the symptoms associated with FM, consistent with strong correlations observed between pain and fatigue in this condition. In support of malate as a potential biomarker, one small study showed that treatment of individuals with FM with magnesium malate improved FM symptoms using an open label, non-placebo controlled design, while another study showed changes in malate dehydrogenase using proteomic analysis of cerebrospinal fluid from individuals with FM compared to healthy controls. These studies support the hypothesis that malate may have a connection to the disease itself.

An e analysis was performed on plasma samples collected as part of the Fibromyalgia Activity TENS Study. The primary aim of this was a randomized clinical trial to investigate effects of TENS on pain in fibromyalgia. During the course of this study a subpopulation of individuals, and a matched cohort of healthy controls, provided plasma samples. This plasma was used to examine metabolites indicative of fibromyalgia.

To assess and validate candidate metabolic biomarkers in a large cohort of individuals, samples were collected from a large NIH-funded cohort study (CORT) that extensively phenotyped subjects with primary FM, healthy controls (HC), and 3 other chronic pain conditions: osteoarthritis (OA), carpal tunnel syndrome (CTS), and rheumatoid arthritis (RA). This allowed for a determination of whether changes in malate or other candidate metabolite biomarkers were specific for primary FM, also occur in those with secondary FM, or are ubiquitous across chronic pain conditions.

Aim 1: Characterize diagnostic test metrics for candidate biomarkers using receiver operating characteristic curves (ROCs), i.e. sensitivity and specificity, and test-retest reliability, to correctly identify individuals with FM from healthy controls and other degenerative, neuropathic, and inflammatory pain conditions: OA, CTS, and RA.

Aim 2: Determine associations between putative metabolite biomarkers and multiple self-reported symptom domains in those with FM: a) pain; b) fatigue; c) sleep; d) physical function; e) psychological factors, and f) disease impact/disability.

Malate and 17 additional putative biomarkers were identified that may serve as diagnostic or within-disease phenotype identifiers. These biomarkers may provide for a diagnostic, and potentially a therapeutic, biomarker associated with cell metabolism. Identification of a disease-specific biomarker allows for a major clinical advance in the diagnosis of individuals with FM which leads to earlier treatment of the condition, and aids in the development of targeted treatments.

An untargeted approach was used for the discovery of potential metabolites using metabolomics using plasma samples from those with fibromyalgia and healthy controls. Women with fibromyalgia have significantly lower levels of the metabolite, malate, in samples from plasma, when compared to controls. Malate is part of the energy metabolism pathway for cells. In the overall analysis a total of 18 metabolites were significantly different from healthy controls, yet malate was uniquely different with a clear separate from healthy controls and those with fibromyalgia which resulted in excellent sensitivity and specificity. Thus, women with fibromyalgia have significantly lower levels of the metabolite, malate, in samples from plasma, when compared to controls and so malate is the first biological marker that has had a clear and distinct signal in this population.

In summary, a total of 18 metabolites were significantly different from healthy controls, yet malate was uniquely different with a clear separation from healthy controls and those with fibromyalgia which resulted in excellent sensitivity and specificity.

Example 3

Currently, there are no established biomarkers for the diagnosis or symptoms of pain and fatigue in individuals with fibromyalgia (FM). The objective of the study was to identify potential biomarkers in individuals with FM, and to correlate these putative biomarkers with FM-symptoms using a targeted metabolomics approach.

The current study was a secondary analysis from baseline data taken in the Fibromyalgia Activity Study with TENS (FAST). Plasma samples and baseline patient-reported outcomes for resting pain and fatigue were obtained from 59 women with FM (mean+SD; age=49.69±11.54, BMI=35.23±10.91) matched with 38 healthy controls (HC) (age=51.0±11.46, BMI=32.33±8.66). Serum/plasma metabolomic extracts were derivatized and analyzed by gas chromatography mass spectrometry for 63 key metabolites representing the tricarboxylic acid cycle, glycolysis, pentose phosphate pathway, amino acid metabolism, neurotransmission, reactive oxygen species defense, and energetics. Differences between FM and HC were assessed for each metabolite using unpaired t-tests (corrected $p<0.008$) and Pearson's correlation coefficients were assessed between significant metabolites and baseline pain and fatigue.

Ten of the 63 metabolites showed significant between-group differences ($P<0.0001$). 2-hydroxybutyrate, asparagine, cysteine, fumarate, histidine and tryptophan were negatively correlated with pain and fatigue ($P=0.002$ to $0.0001$, $r=-0.315$ to $-0.894$) while 6-phosphogluconate, hypoxanthine, and sphingosine were positively correlated ($P=0.004$ to $0.0001$, $r=0.291$ to $0.366$).

The results of this study demonstrate individuals with FM have different resting levels of a variety of metabolites compared to HC, which correlate with their symptoms. These metabolites are generally involved in reduction-oxidation pathways and energy metabolism. Future work will confirm these findings in a new cohort and examine if interventions can alter these metabolites and symptomology.

Example 4

Differences in FM and other patient conditions associated with chronic pain: carpal tunnel syndrome (CTS, neuropathic), rheumatoid arthritis (RA, nociceptive/inflammatory), and osteoarthritis (OA, nociceptive/degenerative) were determined to more clearly differentiate whether the identified biomarkers were generically related to pain or specific to FM. in a large sample of pain cohorts and matched healthy controls (the CORT study), which is a well characterized study population to analyze stored blood samples. Further, subpopulations of these individuals with degenerative, inflammatory, and neuropathic pain conditions also meet criteria for FM, termed secondary FM. The currently collected sample from the CORT shows 25% of RA, 15% of carpal tunnel, and 5% of hip OA subjects meet criteria for FM. The study also examines repeatability of the biomarker over time in a separate sample of individuals with FM.

Use of a targeted metabolomics approach provides insights into mechanisms underlying FM and other chronic pain conditions. The primary outcome and aims focus on a single metabolite, malate, that has strong separation between FM and healthy controls with excellent sensitivity and specificity, as shown in preliminary data. Up to 17 additional metabolites are evaluated using a targeted metabolomics approach to analyze plasma samples using a panel of metabolites.

The samples from the CORT study provide reliable and robust phenotyping data on subjects across multiple domains as CORT blood samples were collected from an extensively phenotyped population.

The study comprehensively phenotypes subjects across multiple domains: pain, fatigue, sleep, physical activity and psychological co-morbidities. Moderate differences in putative biomarkers are characterized and it is determined if individual metabolites are related to specific symptom domains of FM. Metabolite clusters/biosignatures are examined, e.g., how they relate to symptom domains, and it is determined if symptom clusters are related to metabolite clusters.

Aim 1: Characterize testing metrics for candidate biomarkers using receiver operating curves (ROCs), i.e. sensitivity and specificity, and test-retest reliability, to correctly identify individuals with and without FM from healthy controls and other chronic pain conditions: osteoarthritis, carpal tunnel, and rheumatoid arthritis.

Rationale. FM currently has no established diagnostic biomarkers, often delaying diagnosis and potentially impairing targeted treatment Thus, there is a need for biomarkers for FM that aid in diagnosis, not only to discriminate FM from healthy individuals, but also to discern it from other chronic musculoskeletal pain conditions. The data supports malate as a candidate for a FM metabolic biomarker, as well as several secondary metabolic biomarkers. Malate resulted in a ROC area under the curve (AUC) value of 0.998, producing nearly 100% separation between our FM and matched HC cohorts. Further, 8 additional metabolite biomarkers resulted in ROC AUCs ranging from 0.72 to 0.89 and large effect sizes for differences between FM and HCs (|d|>0.9), to serve as secondary FM biomarker candidates, including: fumarate, cysteine, 6-phosphogluconate, sphingosine, hypoxanthine, asparagine, tryptophan and 2-hydroxybutyrate.

Ideally, a biomarker for FM demonstrates not only high sensitivity and specificity relative to healthy controls, but also differentiates individuals from other chronic musculoskeletal pain conditions. To that end three disease states were selected: OA to represent a common, yet predominantly localized form of degenerative joint arthritis, RA to represent a predominantly systemic, inflammatory arthritis, and carpal tunnel syndrome to represent a neuropathic pain condition. FM is currently diagnosed based on symptomology criteria, whereas OA, RA, and carpal tunnel syndrome have some degree of diagnostic tests available, in addition to symptomology criteria, to aid in their diagnosis. The ability to discriminate FM from other sources of musculoskeletal pain provides opportunities for targeted care.

Aim 2: Determine associations between putative metabolic biomarkers and multiple self-reported symptom domains in those with FM: a) pain; b) fatigue; c) sleep; d) physical function; e) psychological factors, and f) disease impact/disability.

Rationale. Metabolic biomarkers, in addition to serving as diagnostic indicators, have good potential to discriminate individuals within the disease population. Nine candidate biomarkers were identified from preliminary data as producing ROC AUC values of 0.7 or greater, and an additional nine candidate biomarkers showed significant differences between FM and HC cohorts ($p<0.05$) with AUCs ranging from 0.64 to 0.69 (see Table 1). Data in women with FM show that several distinct metabolites are associated with one or more symptomology domains with correlation magnitudes of at least 0.2. For example, malate, serine and aconitate were moderately associated with pain measures, whereas uracil, urea, xanthine and 6-phosphogluconate were moderately associated with fatigue. Notably, the best diagnostic markers, differentiating FM from HC individuals, were not necessarily the same biomarkers demonstrating the strongest relationships with symptom severity within the FM cohort. For example, malate had a high sensitivity and specificity between healthy controls and FM, but only had modest correlations with pain. On the other hand, uracil, urea, xanthine, and 6-phospgulonate were moderately associated with fatigue but have poorer sensitivity and specificity. The identification of metabolic biomarkers that are most closely associated with distinct symptom domains is a step in identifying possible underlying mechanisms that subsequently may improve targeted treatment, be useful as clinical endpoints in future investigational trials, and contribute to identifying subclasses of the condition. Accordingly, Aim 2 evaluates the relationships between 18 blood metabolites and phenotypic characterization of symptom severity within the FM cohort: the nine metabolites identified in Aim 1 as well as the following nine metabolites: histidine; uracil; 1-Octadecanol; aconitate; inositol; phosphoenolpyruvate; urea; serine; and xanthine. More details regarding the candidate metabolite biomarkers are provided in Table 1.

The patient-reported outcomes address multiple domains to phenotype pain; fatigue: sleep; physical and social functioning; disease impact, including disease specific measures; anxiety, depression, catastrophizing, and others.

Figure 4:
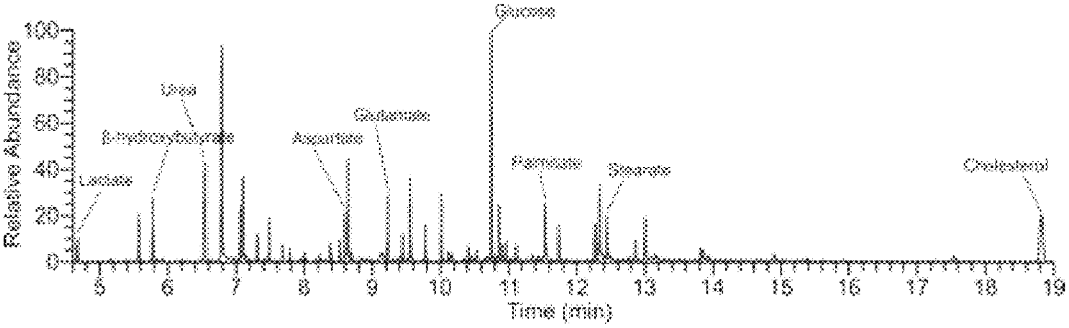
FIG. 4. Example GC-MS Chromatogram. GC-MS chromatogram of liver sample acquired on high resolution Q-Exactive GC-MS.
Figure 5:
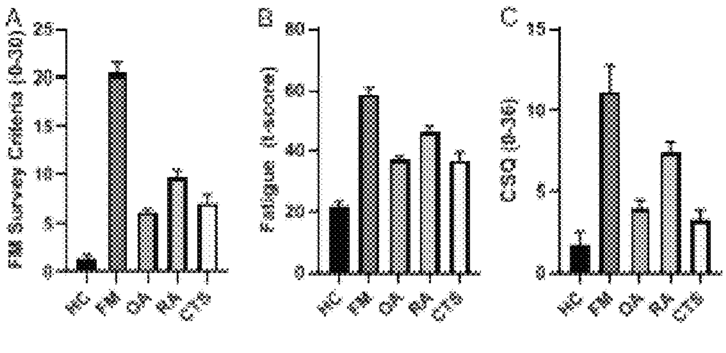
FIG. 5. Phenotype data from 3 outcomes for 5 different populations for the FM Survey Criteria, PROMIS-Fatigue, and the CSQ.

Gas (GC-MS) and liquid (LC-MS) chromatography/mass spectrometry-based targeted metabolomics are applied to biological samples such as tissue, plasma, serum, synovial fluid, and cultured cells (FIG. 4). GC-MS or LC-MS may be employed. The first step is to lyophilize (freeze-dry) samples: serum will be lyophilized and stored at −80° C. For analysis of metabolites, samples are extracted with a methanol-acetonitrile-water mix modified for each sample type. Next, to make metabolites of interest amenable to GC-MS, samples are converted to their trimethylsilyl derivative (Bricker et al., 2012). Metabolites are separated by gas chromatography and detected using either a single quadrupole mass spectrometer (MS) in targeted Selective Ion Monitoring (SIM) mode to maximize sensitivity, with less efficient GCQ-Exactive (QE) MS available for secondary use as a validation method. When utilizing GC-MS, separated metabolites are ionized by electron ionization (EI), which produces fragmentation patterns unique to each molecule and enables clear, highly confident identification. Data is collected in either full mass range (50-700 Da) or by single ion monitoring (SIM), which focuses on selected ions of interest only. To ensure high quality data for metabolite profiling, a set of 9 isotopically labeled internal standards are added prior to sample extraction. These internal standards correct for extraction, derivatization and/or loading effects. Pooled Quality Control QC) samples are injected in duplicate at the beginning and end of each run, as well as after every 10 runs. This is done to correct for instrument drift over time using local regression analysis by NOREVA software (Li et al., 2017). Identification of metabolites in a sample is based on comparison to an in-house mass spectrum library of authentic standards and their retention times (Tier 1) using Tracefinder 4.0 (Thermo) software. This targeted GC-MS protocol identifies and measures more than 100 metabolites. These include citric acid cycle and glycolytic/gluconeogenic intermediates as well as amino acids, sugars, neurotransmitters, and fatty acids (Cantor et al., 2017) (FIG. 5).

Identification of metabolites with targeted GC-MS approach relies on retention time, mass accuracy, and mass spectral comparisons to authentic standards. GC-MS is particularly useful for central carbon metabolism including the citric acid cycle, amino acids, other organic acids, and sugars.

GC-MS is also useful for smaller, thermally-stable molecules and separation is based on volatilities. An advantage of GC-MS protocol for targeted profiling is that retention times for metabolites are reproducible with narrow variation with no need for retention time alignment. GC-MS analysis using electron ionization (EI) is acquired using known standard conditions and produces unique fragmentation patterns or mass spectrum for each molecule. This feature enhances structure determination and allows for efficient library comparisons for confirming identifications. While LC-MS accommodates detection of larger, more thermally-labile compounds, comparison to mass spectra libraries is more difficult for LC-MS, because the ionization process and MS/MS conditions vary from instrument to instrument. Thus, for this study, we will use GC-MS.

Figure 6:
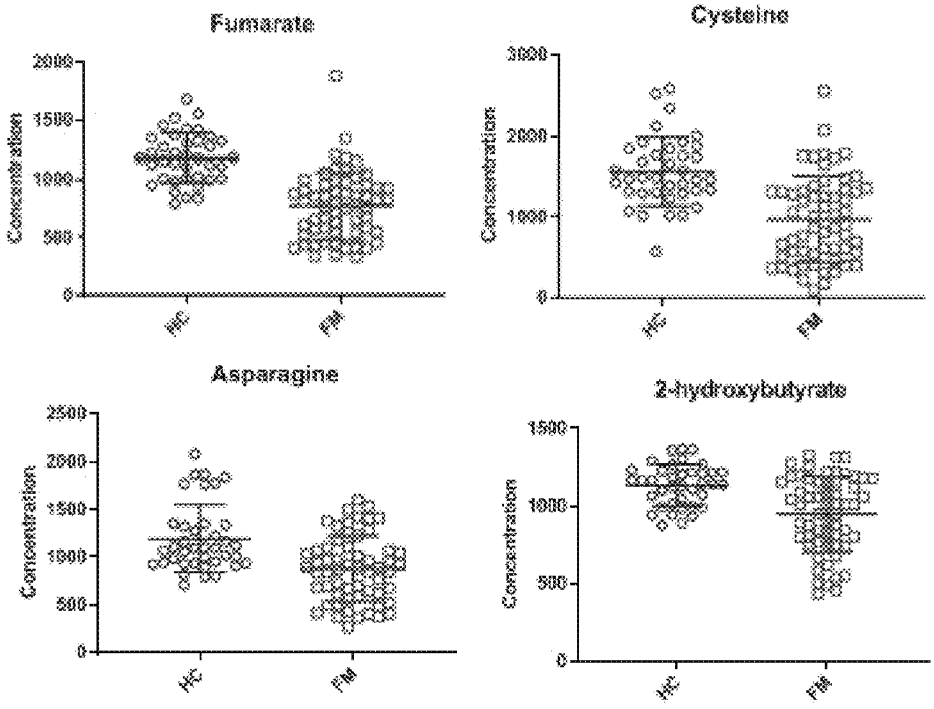
FIG. 6. Scatter plots of four metabolite concentrations for HC (blue) and FM (red) subjects. ($p<0.0001$).
Figure 7:
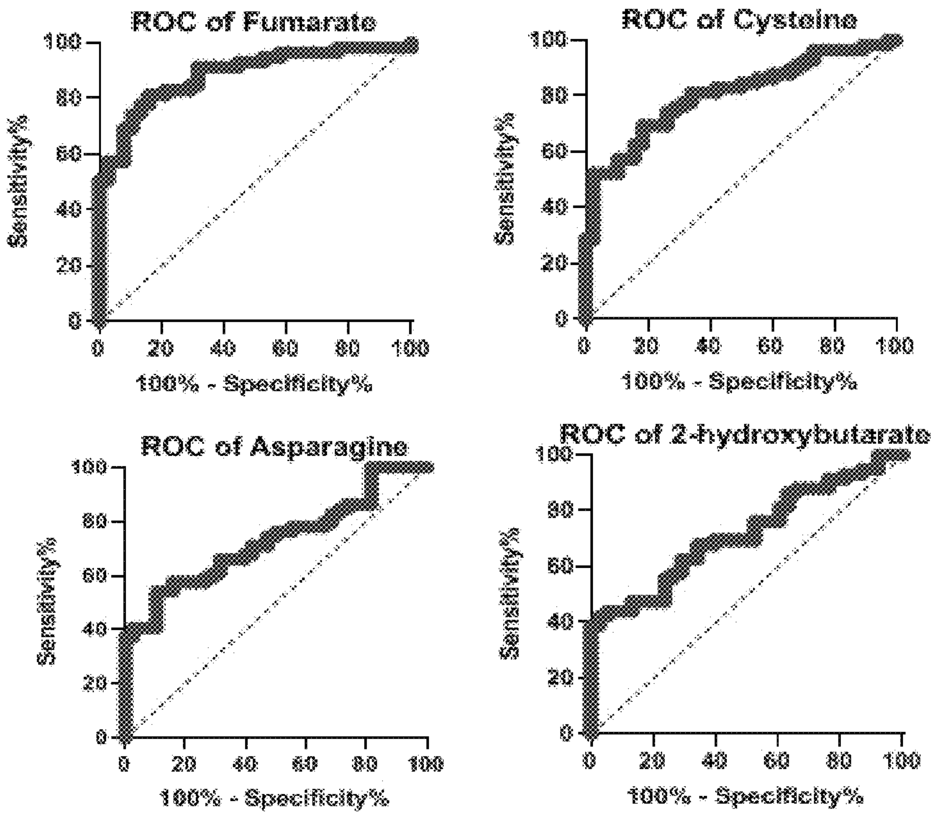
FIG. 7. ROC curves for FM diagnosis based on four metabolites.
Figure 8:
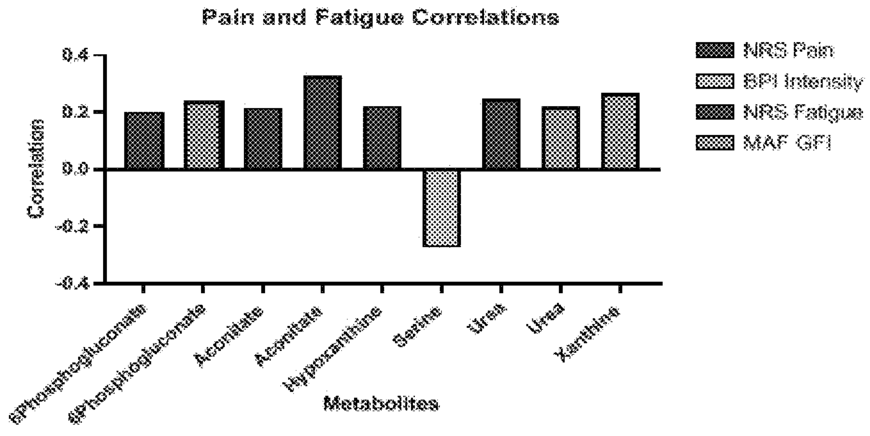
FIG. 8. R-value between FM metabolite concentrations and pain and fatigue measures. ($R>0.2$ shown).
Figure 9:
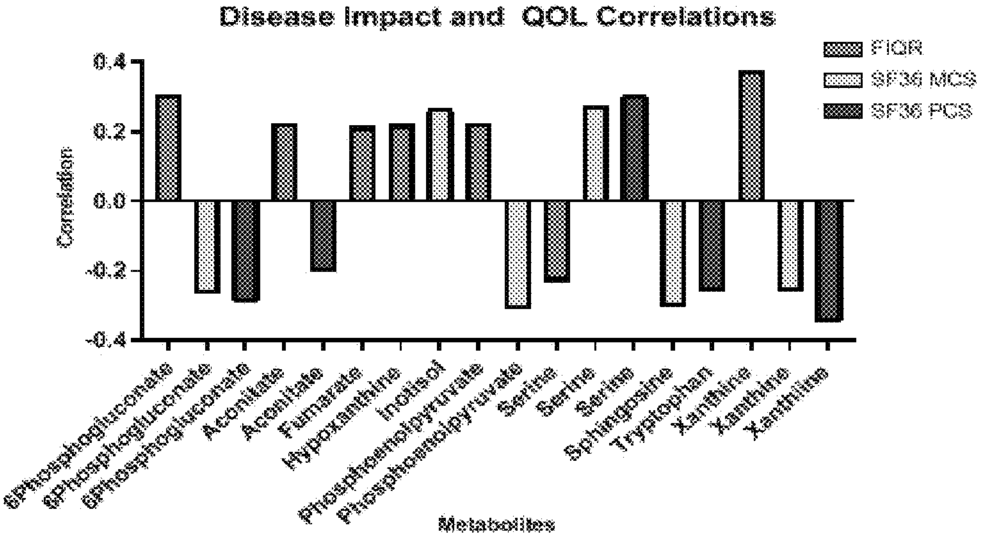
FIG. 9. R-values between FM metabolite concentrations and measures of disease impact and QOL ($r>0.2$).
Figure 10A:
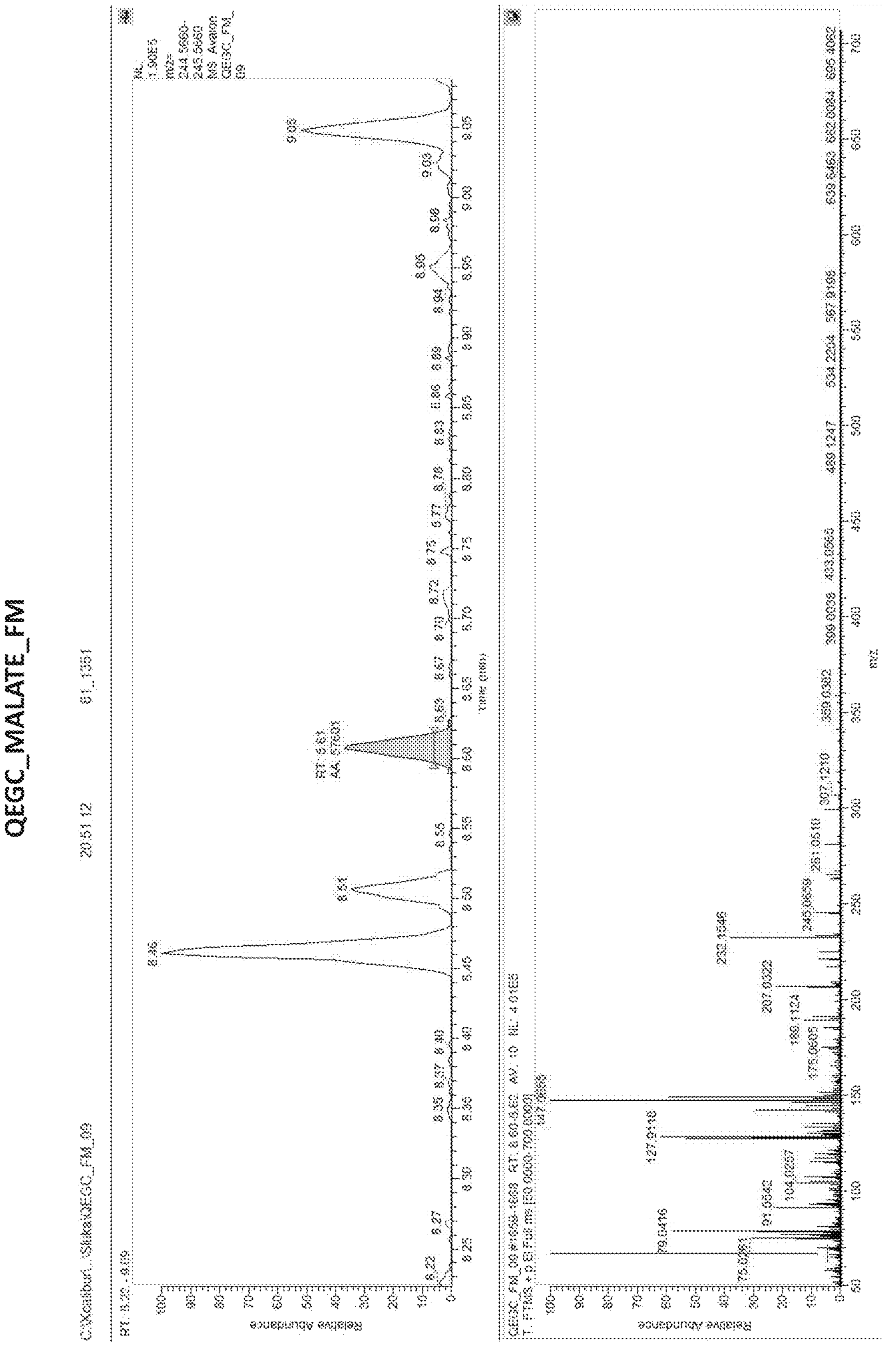
FIGS. 10A-10H. Traces of malate and fumarate in FM and control patients using two different methods for mass spectrometry.
Figure 10B:
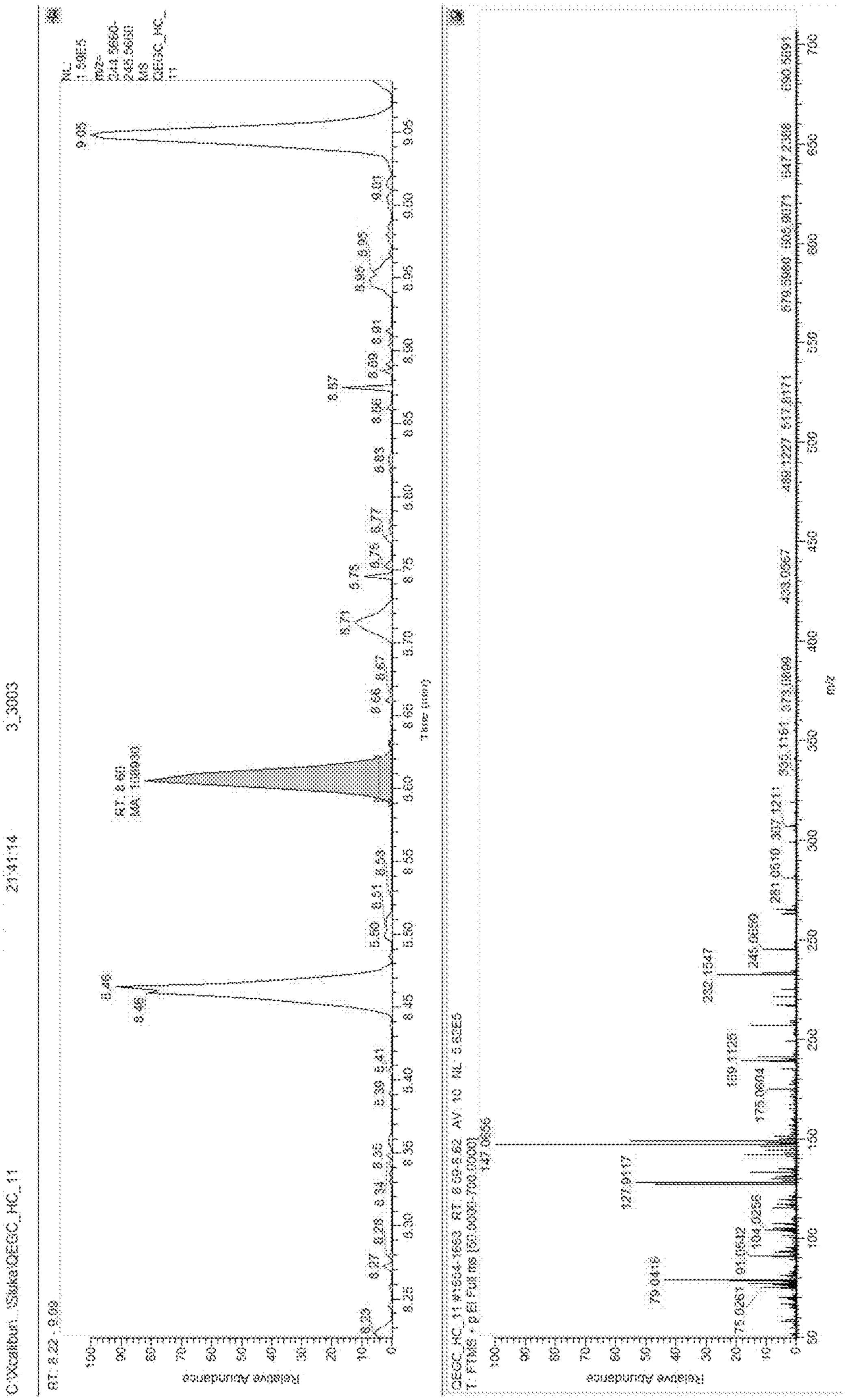
Figure 10C:
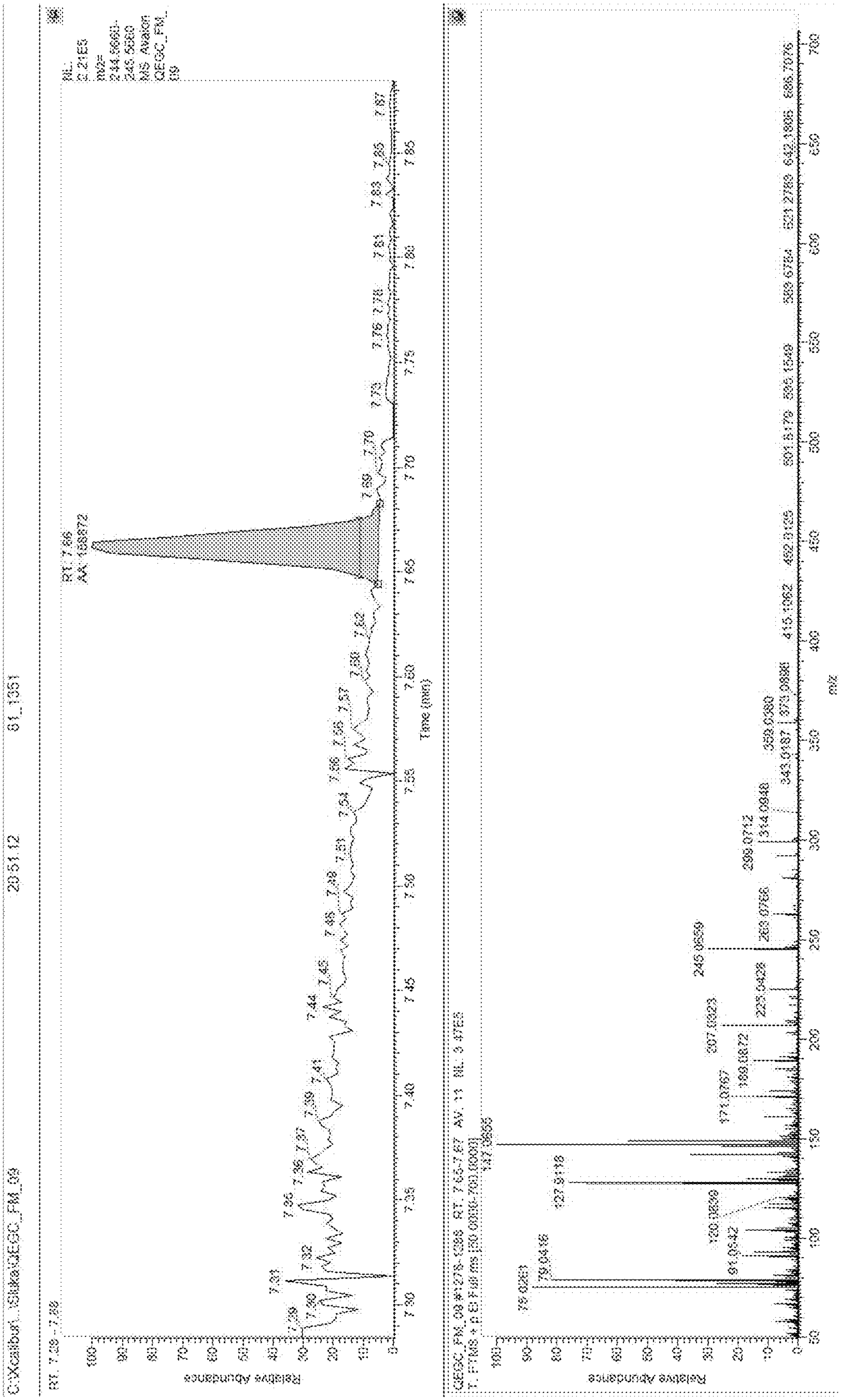
Figure 10D:
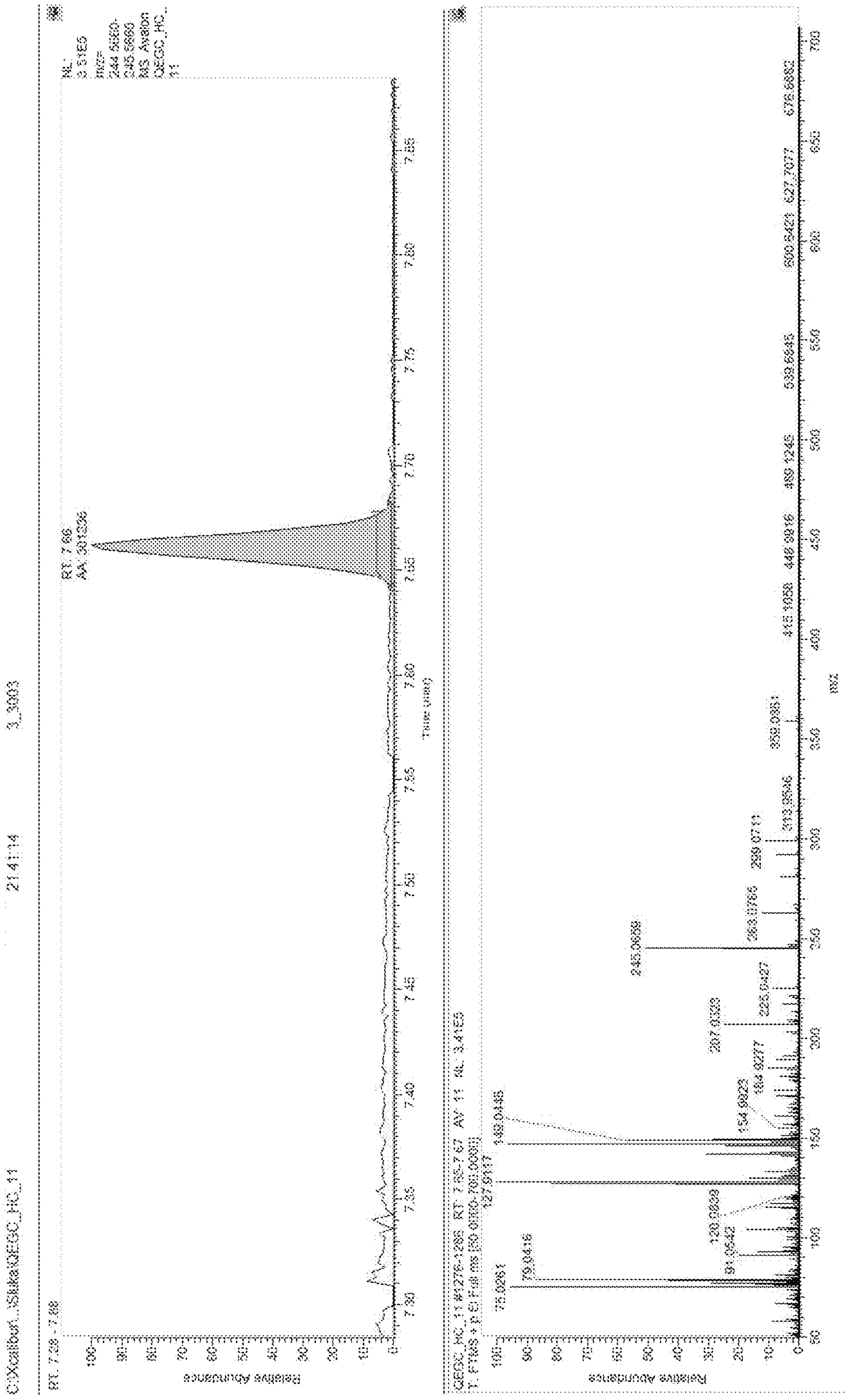
Figure 10E:
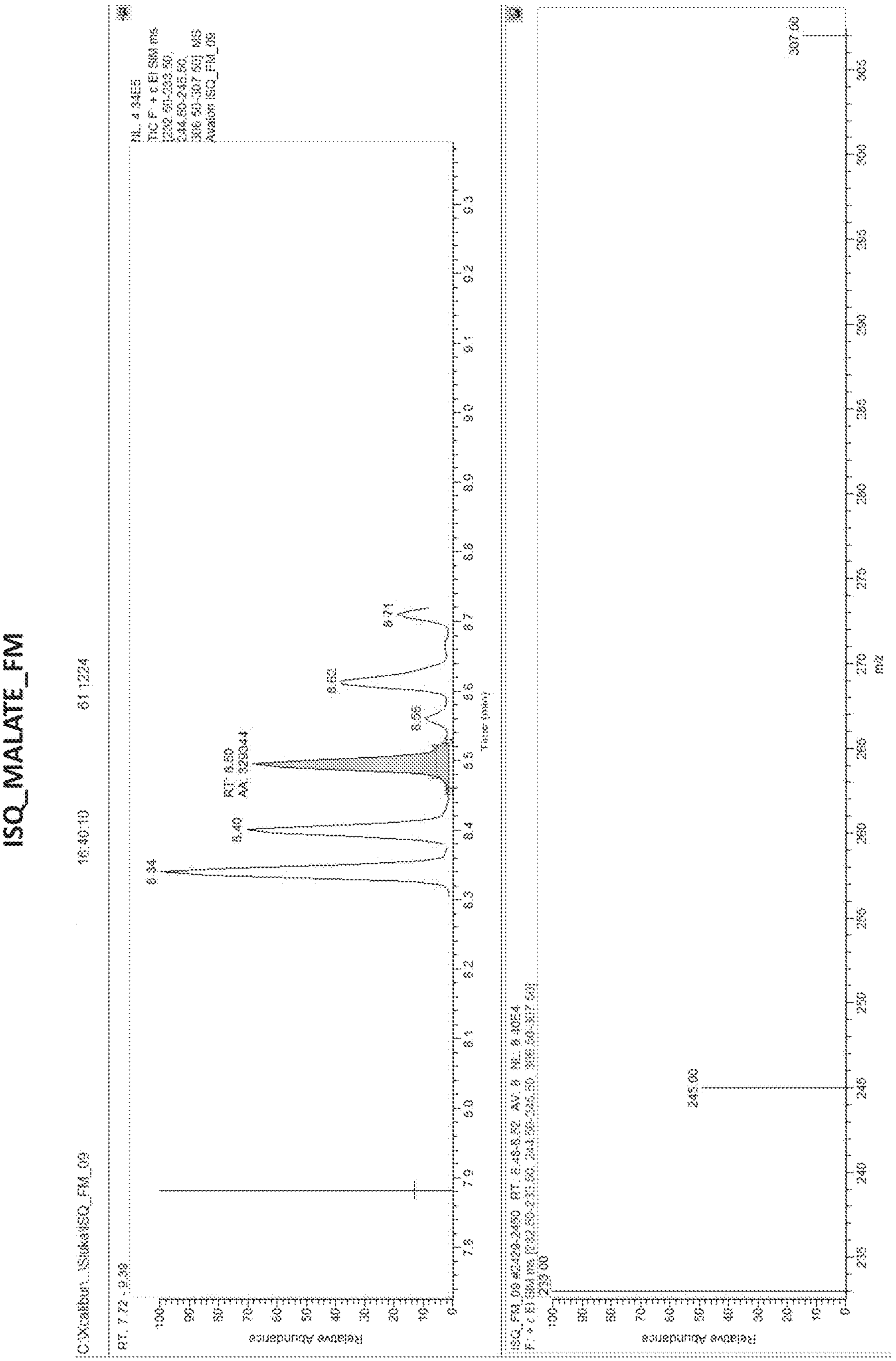
Figure 10F:
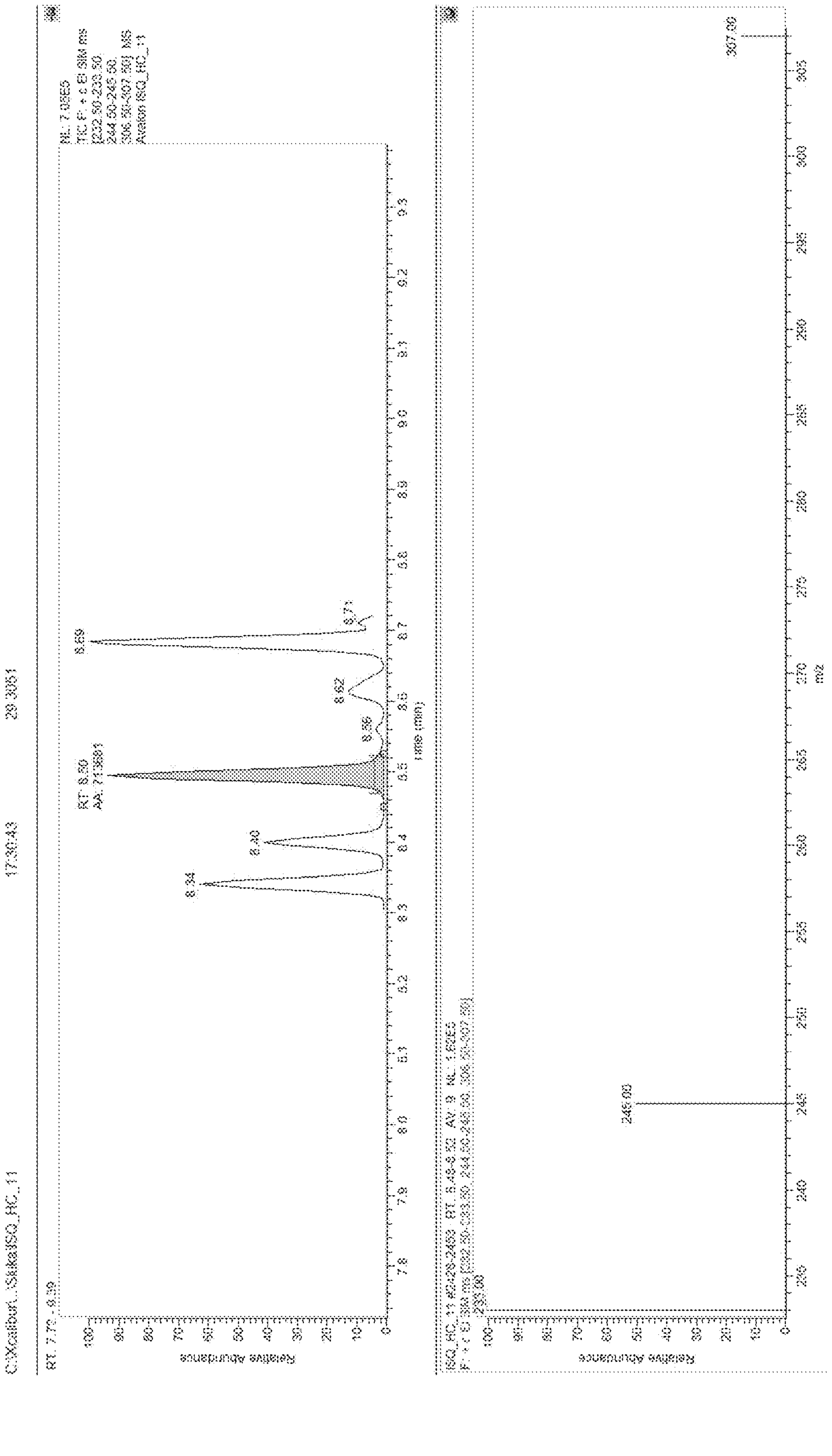
Figure 10G:
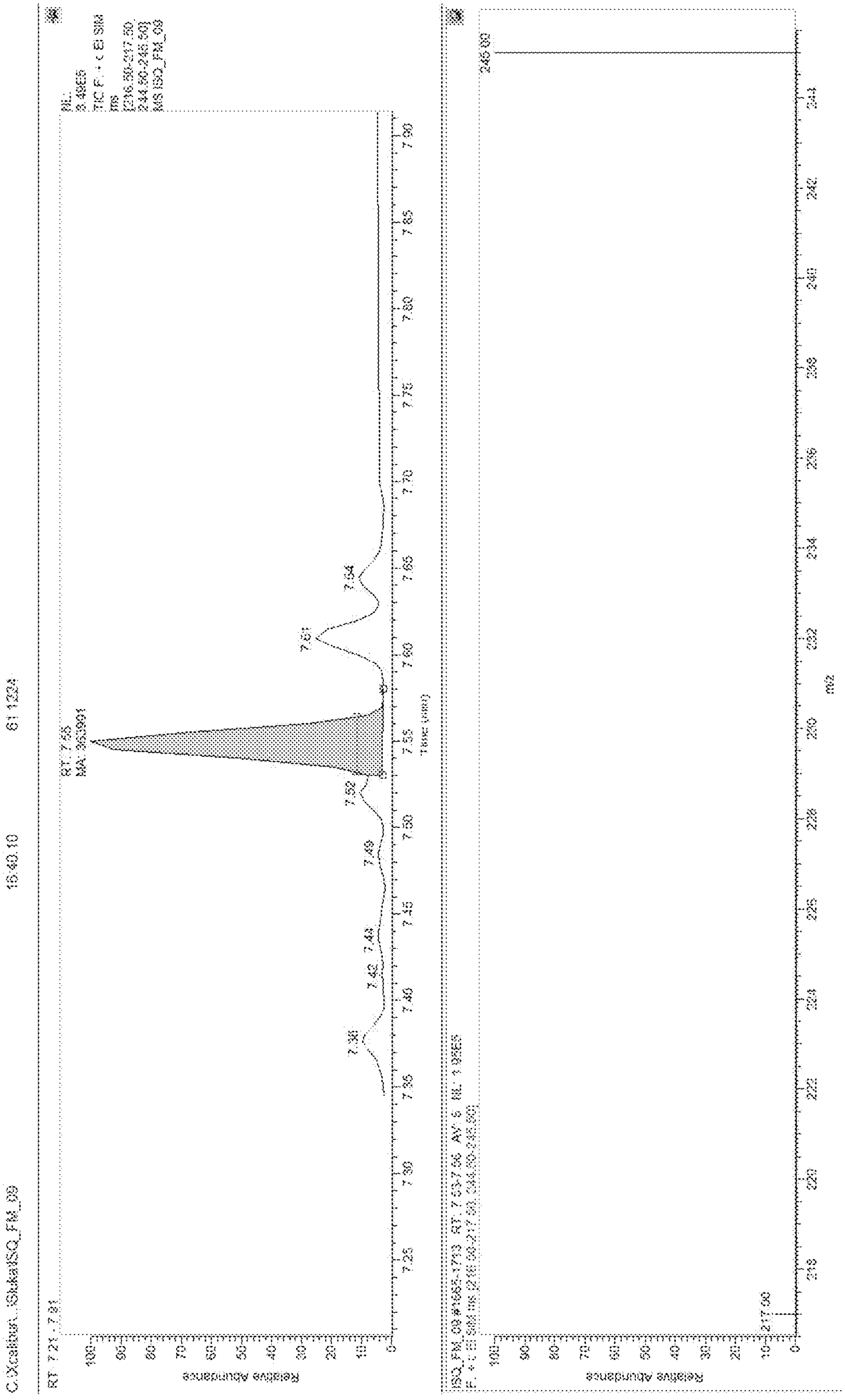
Figure 10H:
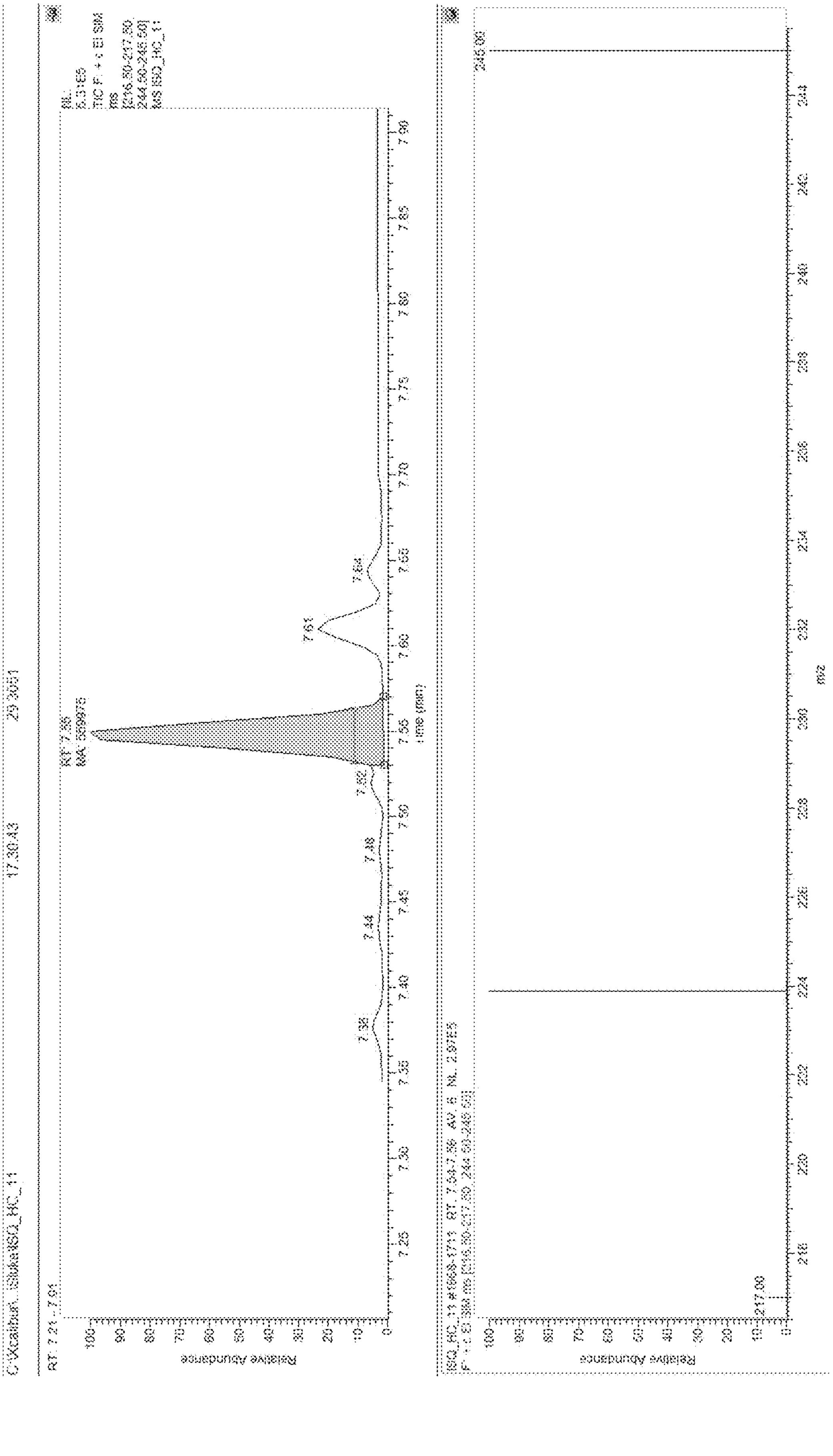

The CORT study has already enrolled nearly 250 participants across the 5 cohorts (FIG. 6).

Statistical Analyses. Continuous variables are summarized as mean±SD or median±interquartile ranges (IQR) based on data distribution by cohort (FM, RA, OA, CTS, HC) and sex (M,F). If needed, Box-Cox transformations are performed to satisfy distributional assumptions. Significance is set at p≤50.05, unless otherwise noted, and performed using SAS statistical software.

Aim 1 Analyses: Data from all 5 subgroups (FM, OA, RA, CTS, HC), from both sites (Michigan and Iowa) are included for Aim 1 analyses. Receiver Operating Curves (ROC) of sensitivity and (1-specificity) are assessed for each of the 9 targeted metabolites identified for Aim 1 (see Table 1) first for FM (primary) vs HC cohorts only. Second, those with primary+secondary FM (FM score≥13) are assessed relative to all others (HC and non-secondary FM cohorts). Third, the ROCs for the other three pain conditions (OA, RA, CTS) relative to HCs are assessed secondarily. The ROC area under the curve (AUC) statistic ks assessed as the primary quantitative outcome from the ROC analyses (where AUC=0.5 is no better than 50:50 chance and 1.0 is a perfect diagnostic indicator). Significant cohort differences in each serum metabolite relative concentration (from GC-MS) between all cohorts (FM, OA, RA, CTS, HC) are determined using analysis of variance (ANOVA), with Box-Cox transformations as needed if normality assumptions are violated (Shapiro-Wilk test and Q-Q plots). Adjusted p-values are assessed using the False Discovery Rate correction to reduce likelihood of both type I and type II errors. Unadjusted and adjusted analyses (sex, age, BMI, and FM score) are performed to further evaluate the degree to which secondary FM (i.e., high FM score) is associated with metabolite concentrations. Total targeted sample size between both sites is as follows: n=100 (FM); 100 (HC); 70 (hip OA); 70 (CTS); and 70 (RA) in approximately equal proportions of males and females, for a total of 410 participants. Of the 210 non-FM pain conditions, ~n=30-35 exhibit secondary FM, based on current CORT proportions. The CORT study is approaching their half-way mark for recruitment and has blood draws performed on between 77-90 per cohort. Data from the first visit for Iowa samples are used for the above analyses. Six- to eight-week test-retest stability for the Iowa cohort (n=60) is assessed using intra-class correlations (ICC, 2-way mixed effects model, with single measurement, and absolute agreement). ICCs (with 95% confidence intervals) <0.5; 0.5-0.75; 0.75-0.9; and >0.9 are defined as having poor, moderate, good, and excellent reliability, respectively.

TABLE 3

No Differences in Physical Activity Levels Between Groups

| PA Outcome | FM (n = 57-59) Mean | FM SD | HC (n = 28-38) Mean | HC SD | Cohen's d | P-value |
|---|---|---|---|---|---|---|
| MVPA (min/day) † | 77.98 | 83.63 | 86.77 | 48.98 | −0.13 | 0.61 |
| VO2 * min (AUC) † | 7236 | 1083 | 7402 | 843 | −0.17 | 0.48 |
| Mean METs † | 2.36 | 0.37 | 2.36 | 0.30 | 0.01 | 0.96 |
| Steps/week † | 72078 | 29824 | 81013 | 25729 | −0.32 | 0.13 |
| IPAQ MET * min/week | 2312 | 2373 | 2777 | 1928 | −0.22 | 0.31 |

Aim 2 Analyses: The 18 putative FM metabolite biomarkers (Table 1) are correlated with multiple domains of FM symptomology in the FM cohort only (primary FM) and in combination with those with high FM scores (primary+secondary FM): pain (BPI, mean daily pain intensity); fatigue (PROMIS); sleep (PROMIS); disease impact (FIQ-R), self-reported physical and social function (PROMIS), pain catastrophizing (CSQ) and depression (HADS) using Pearson Correlation Coefficients. Data are log transformed as needed prior to analyses (or other appropriate Box Cox transformations to ensure normal distributional assumptions are valid). Correlational analyses, mediated by sex, are also considered, to examine if the putative biomarkers demonstrate notable sex differences. Separate analyses by sex are performed if mediation effects are noted. Unadjusted and adjusted analyses controlling for self-reported age and BMI will be evaluated. Temporal associations between biomarkers and symptomology are assessed secondarily using change scores for metabolite and phenotype variables. When phenotypes vary significantly overall (mean change score different than zero), significant Pearson correlation coefficients between changes in metabolites and changes in symptomology are used to identify how metabolite concentrations and symptoms co-vary.

Results

Based on preliminary data, excellent sensitivity and specificity for malate in FM compared to healthy controls is observed. Moreover, malate differentiates between other pain conditions with secondary FM and non-FM pain conditions. It is possible, however, that malate be a general biomarker for pain.

Example 5

Biomarkers are commonly used in clinical research to diagnosis and predict clinical outcomes for an assortment of populations. Currently, there are no established biomarkers for the diagnosis of fibromyalgia (FM) or the common symptoms associated with this disease. By identifying specific biomarkers for FM, we can improve diagnostic criteria, gain a better understanding into the mechanisms of symptom development, and improve clinical endpoints for future interventional trials.

The objectives were to 1) identify differences in specific biomarkers between individuals with FM and healthy controls, and 2) determine correlations between biomarkers and common symptoms of FM, including pain, fatigue, disease impact and quality of life (QoL).

Metabolic profiles may differ between women with and without fibromyalgia, thus will serve as diagnostic and symptomology disease biomarkers.

Participants:

Women with FM, n=59, and sex, age, and BMI matched controls (HC), n=38 (Table 4).

TABLE 4

Participant Characteristics

| | FM (n = 59) | HC (n = 38) |
|---|---|---|
| Age (years) | 49.7 ± 11.5 | 51.0 ± 11.5 |
| BMI (kg/m$^2$) | 35.2 ± 10.9 | 32.3 ± 8.7 |

Protocol:

Secondary analysis from baseline data of the Fibromyalgia Activity Study with TENS (FAST) (NCTO1888640)

Analyzed serum/plasma samples and baseline patient-reported outcomes for resting pain and fatigue, Fibromyalgia Impact Questionnaire (FIQR), Multidimensional Assessment of Fatigue Global Fatigue Impact (MAF GF), Brief Pain Inventory (BPI) Intensity, and Short Form 36 (SF36) Mental Component Summary (MCS) and Physical Component Summary (PCS)

Serum/plasma metabolomic extracts were derivatized and analyzed by gas chromatography mass spectrometry for 63 key metabolites representing the tricarboxylic acid cycle, glycolysis, pentose phosphate pathway, amino acid metabolism, neurotransmission, reactive oxygen species defense, and energetics (ISQ single quadrapole GC-MS & QE GC orbitrap mass spectrometer)

Statistical Analysis:

Differences between FM and HC were assessed for each metabolite using unpaired t-tests (corrected $p<0.008$)

Receiver operator curves (ROC) were used to assess the diagnostic accuracy of each metabolite between FM and HC.

Pearson's correlation coefficients were assessed between significant metabolites and baseline patient reported outcome measures (log transformed); pain, fatigue, FIQR, MAF, BPI, PCS and MCS

TABLE 5

Metabolite Concentrations (mean ± SD) for FM and HC. Significant differences found for 9 of 63 metabolites tested ($p < 0.008$)

| Metabolite | FM | HC | P-value |
|---|---|---|---|
| 2-Hydroxybutyrate | 949.4 ± 243.5 | 1134.1 ± 21.5 | <.0001 |
| 6-Phosphogluconate | 1024.3 ± 186.6 | 854.1 ± 854.1 | <.0001 |
| Asparagine | 880.5 ± 343.7 | 1196.4 ± 57.5 | <.0001 |
| Cysteine | 974.7 ± 535.1 | 1561.2 ± 68.7 | <.0001 |
| Fumarate | 773.4 ± 289.4 | 1182.8 ± 34.3 | <.0001 |
| Histidine | 950.6 ± 296.5 | 1202.7 ± 57.3 | .0002 |
| Hypoxanthine | 1103.4 ± 251.3 | 918.1 ± 33.1 | .0002 |
| Sphingosine | 1005.3 ± 283.7 | 773.6 ± 47.3 | .0001 |
| Tryptophan | 925.7 ± 216.4 | 1102.8 ± 31.4 | <.0001 |

CONCLUSIONS

The results of this study demonstrate individuals with FM have different resting levels of multiple metabolites compared to HC: several of which correlate with their symptoms, supporting our initial hypothesis.

These metabolites are generally involved in reduction-oxidation pathways and energy metabolism.

The metabolomic profile of other chronic pain conditions such as RA or OA are assessed to see if these metabolite differences are specific to FM

REFERENCES

Bartlett et al., *PLoS One,* 10:e0138543 (2015).
Bellamy et al., *J. Rheumatol.,* 15:1833 (1988).
Bengtsson et al., *Arthritis Rheum.,* 29:817 (1986).
Bennett et al., *Arthritis Res. Ther.,* 11:R120 (2009).
Bricker et al., *Science,* 337:96 (2012).
Brummett et al., *Anesthesiology,* 119:1434 (2013).
Brummett et al., *Arthritis Rheumatol.,* 67:1386 (2015).
Buchwald et al., *Rheum. Dis. Clin. North Am.,* 22:219 (1996).
Caboni et al., *PloS one,* 9:e107626 (2014).
Cantor et al., *Cell,* 169:258 (2017).
Choy et al., *BMC Health Serv. Res.,* 1.0:102 (2010).
Chung et al., *J. Hand Surg. Am.,* 23:575 (1998).
Clauw, J. American Med. Assn., 311:1547 (2014).
Cleeland & Ryan, *Ann. Acad. Med. Singapore,* 23:129 (1994).
Cohen et al., *J. Health Soc. Behav.,* 24:385 (1983).
Cook et al., *Neurology,* 80:S49 (2013).
Cordero et al., *Arthritis Res. Ther.,* 12:R17 (2010).
Dunn et al., Metabolomics, _:_(2013).
Gauffin et al., *BMC Neurol.,* 13:21 (2013).
Group BDW, *Clin. Pharmacol. Ther.,* 69:89 (2001).
Groven et al., *Brain Behav. Immun.*, _:_(2019).
Hackshaw et al. *Analyst,* 138:4453 (2013).
Hackshaw et al., *J. Biol. Chem.,* 294:2555 (2019).
Hauser & Fitzcharles, *Dialogues Clin. Neurosci.,* 20:53 (2018).
Heidari et al., Rheumatol. Int., 37:1527 (2017).
Janda et al., *Anesthesiology.* 122:1103 (2015).
Kalyan-Raman et al., *J. Rheumatol.,* 11:808 (1984).
Khoonsari et al., *J. Proteomics,* 190:35 (2019).
Koo & Li, *J. Chiropr. Med.,* 15:155 (2016).
Kratz et al., *J. Pain,* 16:527 (2015).
Li et al., *Nucleic Acids Res.,* 45:W162 (2017).
Lindh et al., *Scand. J. Rheumatol.,* 24:34 (1995).
Lund et al., *Scand. J. Rheumatol.,* 15:165 (1986).
Macfarlane et al., *Ann. Rheum. Dis.,* 76:318 (2017).
Malatji et al., *BMC Neurol.,* 17:88 (2017).
McGraw & Wong, *Psychological Methods,* 1:30 (1996).
Mendieta et al., *J. Neuroimmunol.,* 290:22 (2016).
Merriwether et al., *Pain Med.,* 18:1485 (2016).
Natelson, *Clin. Ther.,* 41:612 (2019).
Oaklander et al., *Pain,* 154:2310 (2013).
Okifuji & Hare, *Pain Ther.,* 2:87 (2013).
Olausson et al., *J. Pain Res.,* 9:345 (2016).
Olausson et al., *Sci. Rep.,* 5:11894 (2015).
Portney & Watkins, 3rd edition, revised. ed. Upper Saddle River, N.J.: Pearson/Prentice Hall; (2015).
Rosenstiel & Keefe, *Pain,* 17:33 (1983).
Russak et al., *Arthritis Rheum.,* 49:798 (2003).
Russell et al., *J. Rheumatol.,* 22:953 (1995).
Serra et al., *Ann. Neurol.,* 75:196 (2014).
Sluka & Clauw, *Neurosci.,* 338:114 (2016).
Sprott et al., *Ann. Rheum. Dis.,* 63:245 (2004).
Srikuea et al., *Arthritis Rheum.,* 65:519 (2013).
Strimbu & Tavel, *Curr. Opin. HIV AIDS,* 5:463 (2010).
Turunen et al., *Biochim. Biophys. Acta.,* 1660:171 (2004).
Uceyler et al., *BMC Musculoskelet. Disord.,* 12:245 (2011).
Uceyler et al., *Brain,* 136:1857 (2013).
Vincent et al., *BMJ Open,* 5:e006681 (2015).
Wahlen et al., *Front Psychol.,* 9:2400 (2018).
Wells et al., *Ann. Rheum. Dis.,* 68:954 (2009).
Wolfe et al., *Semin. Arthritis Rheum.,* 46:319 (2016)
Wolfe, *Arthritis Care Res.* (*Hoboken*), 63:1073 (2011).
Yunus et al., *Am. J. Med.,* 81:38 (1986).
Zigmond & Snaith, *Acta Psychiatr. Scand.,* 67:361 (1983).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to diagnose and treat fibromyalgia in a mammal, comprising:

determining the amount of malate or fumarate in a physiological sample from the mammal, wherein a decreased amount of malate or fumarate in the sample relative to the amount of malate or fumarate in a corresponding mammal that does not have fibromyalgia is indicative of fibromyalgia, administering to the mammal having decreased malate or fumarate levels an amount of Lyrica, Cymbalta, gabapentin, savella, tramadol, cyclobenzaprine, duloxetine, milnacipran, amitriptyline, pregabalin, trazodone, meloxicam, gualfenesil, topamax, armodafinil, dresaryl, nabilone, prednisone, topiramate, escitalopram, naltrexone, venlafaxine, metaxalone, fluoxetine, sodium oxybate, atomoxetine, desvenlafaxine, Desyrel dividose, topiragen or metaxail.

2. The method of claim 1 wherein the mammal is a human.

3. The method of claim 1 wherein the sample is a blood sample.

4. The method of claim 1 wherein the sample is a plasma sample.

5. The method of claim 1 wherein the sample is a serum sample.

6. The method of claim 1 wherein the amount of presence of malate is determined using an enzymatic assay.

7. The method of claim 1 wherein the amount of malate in the sample is determined to be below 10 μM.

8. The method of claim 1 wherein the amount of fumarate in the sample is less than 1 μM.

9. The method of claim 1 wherein the amount of malate and at least one of fumarate, cysteine, or 6-phosphogluconate is determined.

10. The method of claim 1 wherein the malate is determined using a colorimetric assay.

11. The method of claim 1 wherein the sample is subjected to mass spectrometry or chromatography prior to determining the amount of malate.

12. The method of claim 1 wherein mass spectrometry or chromatography is employed to determine the amount of malate.

13. A method to distinguish pain resulting from fibromyalgia from other disorders, comprising:

providing an amount of malate or fumarate in a physiological sample from a mammal having pain; and determining whether the amount of malate or fumarate in the sample is reduced relative to the amount of malate or fumarate in a corresponding mammal that does not have fibromyalgia, wherein decreased levels of malate or fumarate in the mammal having pain is indicative that the mammal has pain due to fibromyalgia, administering to the mammal having decreased malate or fumarate levels an amount of Lyrica, Cymbalta, gabapentin, savella, tramadol, cyclobenzaprine, duloxetine, milnacipran, amitriptyline, pregabalin, trazodone, meloxicam, gualfenesil, topamax, armodafinil, dresaryl, nabilone, prednisone, topiramate, escitalopram, naltrexone, venlafaxine, metaxalone, fluoxetine, sodium oxybate, atomoxetine, desvenlafaxine, Desyrel dividose, topiragen or metaxail so as to treat the fibromyalgia.

14. A method of monitoring fibromyalgia progression or severity in a mammal, comprising:

providing an amount of malate in a physiological sample from a mammal having fibromyalgia overtime; and determining the amount of malate over time in the mammal having fibromyalgia, wherein a decrease over time is indicative of progression or of an increase in severity of fibromyalgia, administering to the mammal having decreased malate levels an amount of Lyrica, Cymbalta, gabapentin, savella, tramadol, cyclobenzaprine, duloxetine, milnacipran, amitriptyline, pregabalin, trazodone, meloxicam, gualfenesil, topamax, armodafinil, dresaryl, nabilone, prednisone, topiramate, escitalopram, naltrexone, venlafaxine, metaxalone, fluoxetine, sodium oxybate, atomoxetine, desvenlafaxine, Desyrel dividose, topiragen or metaxail so as to treat the fibromyalgia.

15. A method of inhibiting or treating pain in a mammal, comprising:

determining whether a mammal with pain has decreased malate levels relative to a control;

administering to the mammal having pain and decreased levels of malate an effective amount of duloxetine, amitriptyline, pregabalin, trazodone, meloxicam, gualfenesin, topamax, armodafinil, prednisone, milnacipran, topiramate, escitalopram, naltrexone, venlafaxine, metaxalone, fluoxetine, sodium oxybate, atomoxetine, desvenlafaxine, Desyrel dividose, topiragen or metaxail.

16. A method, comprising:

determining whether a mammal has decreased malate levels relative to a corresponding control mammal; and administering to a mammal having decreased malate levels an amount of Lyrica, Cymbalta, gabapentin, savella, tramadol, cyclobenzaprine, duloxetine, milnacipran, amitriptyline, pregabalin, trazodone, meloxicam, gualfenesil, topamax, armodafinil, dresaryl, nabilone, prednisone, topiramate, escitalopram, naltrexone, venlafaxine, metaxalone, fluoxetine, sodium oxybate, atomoxetine, desvenlafaxine, Desyrel dividose, topiragen or metaxail.

17. The method of claim 13 wherein the mammal is a human.

18. The method of claim 13 wherein the amount of malate in the mammal is below 10 μM.

19. The method of claim 15 wherein the mammal is a human.

20. The method of claim 15 wherein the amount of malate in the mammal is below 10 μM.

* * * * *

UNITED STATES PATENT AND TRADEMARK OFFICE

CERTIFICATE OF CORRECTION

PATENT NO. : 12,241,889 B2
APPLICATION NO. : 17/464335
DATED : March 4, 2025
INVENTOR(S) : Kathleen A. Sluka It is certified that error appears in the above-identified patent and that said Letters Patent is hereby corrected as shown below:

In the Specification

In Column 2, Line 33, delete "$1\times10^{6}$" and insert --$1\times10^{-6}$-- therefor In Column 6, Line 8, delete "(mean f SEM;" and insert --(mean±SEM;-- therefor In Column 6, Line 21, delete "mean f SD;" and insert --mean±SD;-- therefor In Column 7, Line 46, delete "LPAQ)." and insert --IPAQ).-- therefor In Column 9, Line 34, delete "90-100%/o" and insert --90-100%-- therefor In Column 9, Table 2, Line 6, delete "75.02% to 93.96%|" and insert --75.02% to 93.96%-- therefor In Column 11, Line 54, delete "(mean+SD;" and insert --(mean±SD;-- therefor In Column 12, Line 63, after "treatment", insert --.--

In Column 13, Line 67, delete "fatigue:" and insert --fatigue;-- therefor

In Column 15, Line 2, delete "p≤50.05," and insert --p≤0.05,-- therefor

In Column 17, Line 4, delete "(NCTO1888640)" and insert --(NCT01888640)-- therefor In Column 17, Line 9, delete "(MAF GF)," and insert --(MAF GFI),-- therefor In Column 17, Line 51, delete "HC:" and insert --HC;-- therefor Signed and Sealed this
Twenty-seventh Day of January, 2026

John A. Squires
*Director of the United States Patent and Trademark Office*

In Column 18, Line 5, delete “1.0:102” and insert --10:102-- therefor

In Column 18, Line 23, delete “*Anesthesiology*.” and insert --*Anesthesiology*,-- therefor In the Claims In Column 20, Line 11, in Claim 14, delete “overtime;” and insert --over time;-- therefor